US008668819B2

(12) United States Patent
Wu et al.

(10) Patent No.: US 8,668,819 B2
(45) Date of Patent: Mar. 11, 2014

(54) UNDERFILL RECOGNITION SYSTEM FOR A BIOSENSOR

(75) Inventors: Huan-Ping Wu, Granger, IN (US);
Joseph E. Perry, Osceola, IN (US);
Christine Trippel, Mishawaka, IN (US);
Eric Maurer, South Bend, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 299 days.

(21) Appl. No.: 12/910,449

(22) Filed: Oct. 22, 2010

(65) Prior Publication Data

US 2011/0108440 A1 May 12, 2011

Related U.S. Application Data

(60) Provisional application No. 61/259,807, filed on Nov. 10, 2009.

(51) Int. Cl.
*G01F 1/64* (2006.01)
*G01N 17/00* (2006.01)
*G01N 27/26* (2006.01)

(52) U.S. Cl.
USPC .... 205/775; 204/403.01; 73/1.02; 205/777.5; 205/792

(58) Field of Classification Search
USPC ............. 204/403.01–403.15; 205/775, 777.5, 205/792; 73/1.02
See application file for complete search history.

(56) References Cited

U.S. PATENT DOCUMENTS

| 4,431,004 | A | 2/1984 | Bessman et al. |
| 5,352,351 | A | 10/1994 | White et al. |
| 5,582,697 | A | 12/1996 | Ikeda et al. |
| 5,620,579 | A | 4/1997 | Genshaw et al. |
| 5,653,863 | A | 8/1997 | Genshaw et al. |
| 6,120,676 | A | 9/2000 | Heller et al. |
| 6,153,069 | A | 11/2000 | Pottgen et al. |
| 6,233,471 | B1 | 5/2001 | Berner et al. |
| 6,391,645 | B1 | 5/2002 | Huang et al. |
| 6,413,411 | B1 | 7/2002 | Pottgen et al. |
| 6,448,067 | B1 | 9/2002 | Tajnafoi |
| 6,531,040 | B2 | 3/2003 | Musho et al. |
| 6,797,150 | B2 | 9/2004 | Kermani et al. |

(Continued)

FOREIGN PATENT DOCUMENTS

| WO | 03091717 | 4/2003 |
| WO | 2005073393 | 8/2005 |

(Continued)

OTHER PUBLICATIONS

International Searching Authority, "International Search Report and Written Opnion for PCT/US2010/053765", Mar. 9, 2011, Publisher: European Patent Office, Published in: EP.

*Primary Examiner* — Luan Van
*Assistant Examiner* — Maris R Kessel
(74) *Attorney, Agent, or Firm* — Blanchard & Associates

(57) ABSTRACT

A biosensor with an underfill recognition system assesses whether to analyze a sample for one or more analytes in response to the volume of the sample. The underfill recognition system applies polling and test excitation signals to the sample. The polling signals generate one or more polling output signals, which maybe used to detect when a sample is present and to determine whether the sample has sufficient volume for analysis. The test excitation signal generates one or more test output signals, which may be used to determine one or more analyte concentrations in the sample.

28 Claims, 9 Drawing Sheets

(56) References Cited

U.S. PATENT DOCUMENTS

| | | |
|---|---|---|
| 7,122,110 B2 | 10/2006 | Deng et al. |
| 7,132,041 B2 | 11/2006 | Deng et al. |
| 7,195,704 B2 | 3/2007 | Kermani et al. |
| 7,351,323 B2 | 4/2008 | Iketaki et al. |
| 7,491,310 B2 | 2/2009 | Okuda et al. |
| 7,537,684 B2 | 5/2009 | Sato et al. |
| 8,002,965 B2 | 8/2011 | Beer et al. |
| 2002/0084196 A1 | 7/2002 | Liamos et al. |
| 2002/0146835 A1 | 10/2002 | Modzelewski et al. |
| 2002/0160517 A1 | 10/2002 | Modzelewski et al. |
| 2004/0256248 A1 | 12/2004 | Burke et al. |
| 2004/0260511 A1 | 12/2004 | Burke et al. |
| 2005/0023154 A1 | 2/2005 | Kermani et al. |
| 2007/0080073 A1* | 4/2007 | Wu et al. .................. 205/777.5 |
| 2008/0173552 A1 | 7/2008 | Wu et al. |
| 2008/0179197 A1 | 7/2008 | Wu |
| 2009/0095071 A1 | 4/2009 | Wu et al. |

FOREIGN PATENT DOCUMENTS

| | | |
|---|---|---|
| WO | 2005078437 | 8/2005 |
| WO | 2006079797 | 8/2006 |
| WO | 2007040913 | 4/2007 |
| WO | WO 2007131036 A1 * | 11/2007 |

* cited by examiner

# UNDERFILL RECOGNITION SYSTEM FOR A BIOSENSOR

REFERENCE TO RELATED APPLICATIONS

This application claims the benefit of U.S. Provisional Application No. 61/259,807 entitled "Underfill Recognition System for a Biosensor" filed Nov. 10, 2009, which is incorporated by reference in its entirety.

BACKGROUND

Biosensors usually analyze a sample of a biological fluid, such as whole blood, urine, or saliva. Samples are compositions that may contain an unknown amount of analyte. Typically, a sample is in liquid form and is an aqueous mixture. A sample may be a derivative of a biological sample, such as an extract, a dilution, a filtrate, or a reconstituted precipitate. A biosensor usually determines the concentration of one or more analytes, a substance present in the sample, such as ketones, glucose, uric acid, lactate, cholesterol, or bilirubin. An analysis determines the presence and/or concentration of the analyte in the sample.

The analysis is useful in the diagnosis and treatment of physiological abnormalities. For example, a diabetic individual may use a biosensor to determine the glucose level in blood for adjustments to diet and/or medication. Biosensors may be underfilled when the sample of the biological fluid is not large enough. An underfilled biosensor may provide an inaccurate analysis of the biological fluid. The ability to identify and prevent these inaccurate analyses may increase the accuracy and precision of the concentration values obtained from the biosensor.

Many biosensors measure an electrical signal to determine the analyte concentration in a sample of the biological fluid. The analyte typically undergoes an oxidation/reduction or redox reaction when an excitation signal is applied to the sample. An enzyme or similar species may be added to the sample to enhance the specificity of the redox reaction. The excitation signal usually is an electrical signal, such as a current or potential. The redox reaction generates an output signal in response to the excitation signal. The output signal usually is another electrical signal, such as a current or potential, which may be measured and correlated with the concentration of the analyte in the sample.

Most biosensors have a measuring device and a sensor strip. A sample of the biological fluid is introduced into a sample chamber in the sensor strip. The sensor strip is placed in the measuring device for analysis. The measuring device applies the excitation signal to electrical contacts connected to electrical conductors in the sensor strip, which typically connect with working, counter, and/or other electrodes that extend into the sample chamber. The electrodes convey the excitation into a sample deposited in the sample chamber. The excitation signal causes a redox reaction, which generates the output signal. The measuring device determines the analyte concentration in response to the output signal.

The sensor strip may include reagents that react with the analyte in the sample of biological fluid. The reagents may include an ionizing agent for facilitating the redox of the analyte, as well as mediators or other substances that assist in transferring electrons between the analyte and the electrodes. The ionizing agent may be an analyte specific enzyme, such as glucose oxidase or glucose dehydrogenase, which catalyze the oxidation of glucose in a whole blood sample. The reagents may include a binder that holds the enzyme and mediator together. A binder is a material that provides physical support and containment to the reagents while having chemical compatibility with the reagents.

Many biosensors include an underfill detection system to prevent or screen out analyses associated with sample sizes that are of insufficient volume. Some underfill detection systems have one or more indicator electrodes that may be separate or part of the working, counter, or other electrodes used to determine the concentration of analyte in the sample. Other underfill detection systems have a third or indicator electrode in addition to the counter and working electrodes used to apply an excitation signal to a sample of the biological fluid. Additional underfill detection systems have a sub-element in electrical communication with the counter electrode. Unlike working and counter electrodes, conductive sub-elements, trigger electrodes, and the like are not used to determine the analyte specific signals generated by the biosensor. Thus, they may be bare conductive traces, conductors with non-analyte specific reagents, such as mediators, and the like.

A biosensor uses the indicator electrodes, third electrodes, or sub-element to detect the partial and/or complete filling of a sample chamber within a sensor strip. Typically, an electrical signal passes between the indicator electrode(s), between the third electrode and the counter electrode, or between the sub-element and the working electrode when a sample is present in the sample chamber. The electrical signal indicates whether a sample is present and whether the sample partially or completely fills the sample chamber. A biosensor using an underfill detection system with a third electrode is described in U.S. Pat. No. 5,582,697. A biosensor using an underfill detection system with a sub-element of the counter electrode is described in U.S. Pat. No. 6,531,040.

While these underfill detection systems balance various advantages and disadvantages, none are ideal. These underfill detection systems usually require additional components, such as the indicator or third electrodes. The additional components may increase the manufacturing cost of the sensor strip and may introduce additional inaccuracy and imprecision due to manufacturing variability. These underfill detection systems also may require a larger sample chamber or reservoir to accommodate the indicator or third electrodes. The larger sample chamber may increase the sample size necessary for an accurate and precise analysis of the analyte. Accuracy includes how close the amount of analyte measured by a biosensor corresponds to the actual amount of analyte in the sample. Accuracy may be expressed in terms of the bias of the biosensor's analyte reading in comparison to a reference analyte reading. Precision includes how close multiple analyte measurements are for the same sample. Precision may be expressed in terms of the spread or variance among multiple measurements.

Additionally, these underfill detection systems may be affected by uneven or slow filling of the sample chamber. The uneven or slow filling may cause these systems to indicate that the sensor strip is underfilled when the sample size is large enough. The uneven or slow filling also may cause these systems to indicate the sensor strip is filled when the sample size is not large enough.

Moreover, these underfill detection systems also may not detect that the sensor strip is underfilled early enough to add more of the biological fluid. The detection may occur after the analysis has started to determine the analytes(s) in the sample. The delay may require replacing the sensor strip with a new sensor strip and a new sample of the biological fluid.

Accordingly, there is an ongoing need for improved biosensors, especially those that may provide increasingly accurate and/or precise detection of underfilled sensor strips and response to underfill conditions. The systems, devices, and methods of the present invention overcome at least one of the disadvantages associated with conventional biosensors.

SUMMARY

An underfill recognition system determines whether a sample of a biological fluid is large enough for an analysis of one or more analytes. The underfill recognition system assesses the volume of a sample to determine whether to stop or proceed with the analysis of one or more analytes in the sample.

In a method for assessing the volume of a sample in a biosensor, a regular polling sequence is applied. The presence of a sample is detected. An extended polling sequence having at least one different extended input pulse is applied. A sample volume sufficient for analysis of at least one analyte in the sample is detected.

In another method for assessing the volume of a sample in a biosensor, a regular polling sequence is applied. When at least one regular output pulse reaches at least one sample threshold is detected. An extended polling sequence is applied. When at least one different extended output pulse reaches at least one volume threshold is detected. When a sample volume is insufficient for analysis of at least one analyte in the sample is indicated. A test excitation signal is applied when the sample volume is sufficient for analysis of at least one analyte in the sample.

A biosensor with an underfill recognition system includes a sensor strip and a measuring device. The sensor strip has a sample interface on a base. The sample interface is in electrical communication with working and counter electrodes positioned in a reservoir formed by the base. The measuring device has a processor connected to a sensor interface. The sensor interface has a signal generator. The sensor interface has electrical communication with the sample interface. The processor directs the signal generator to apply a regular polling sequence. The processor detects the presence of a sample. The processor directs the signal generator to apply an extended polling sequence. The processor detects whether a sample volume is sufficient for analysis of at least one analyte in the sample. The processor directs the signal generator to apply a test excitation signal when a sample volume is sufficient for analysis of at least one analyte in the sample. The processor determines the concentration of at least one analyte in a sample in response to a test output signal.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

Figure 1:
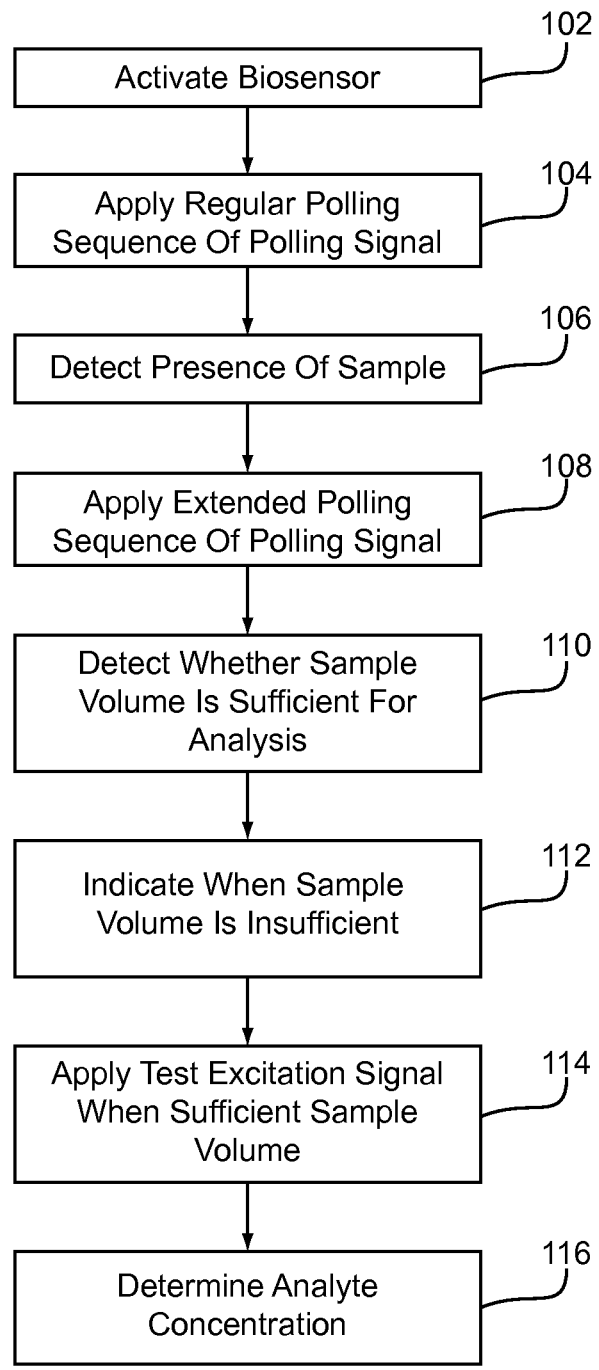
FIG. 1 depicts a method for assessing a sample volume in a biosensor.

An underfill recognition system assesses whether to analyze a sample of a biological fluid for one or more analytes in response to the volume of the sample. The underfill recognition system detects whether a sample is present, determines whether the sample has sufficient volume for analysis, indicates when a sample volume is not sufficient for analysis, and starts or stops the sample analysis in response to the sample volume. The underfill recognition system may improve the accuracy and/or precision of sample analysis by determining whether a sample is large enough prior to analysis.

The underfill recognition system may be implemented on a biosensor or like device. The biosensor applies polling and test excitation signals to a sample. The polling signal generates one or more polling output signals from the sample, which may be used to detect when a sample is present and to determine whether the sample has sufficient volume for analysis. The test excitation signal generates one or more test output signals, which may be used to determine one or more analyte concentrations in the sample. The polling and test excitation signals may be electrical signals, such as potential, current, a combination thereof, or the like. The test excitation signal may be any optical, electrical, or like signal used to determine one or more analytes in the sample. The biosensor may be utilized to determine one or more analyte concentrations, such as glucose, uric acid, lactate, cholesterol, bilirubin, ketone, or the like, in a biological fluid, such as whole blood, urine, saliva, or the like. Other analyte concentrations may be measured including those in other biological fluids.

The polling signal has a regular polling sequence of one or more regular input pulses followed by an extended polling sequence of one or more extended input pulses. Regular input pulses are essentially the same, but different regular input pulses may be used. Regular polling sequences may generate one or more sample output signals when a sample is present in the biosensor. Thus, the sample output signal may be used to detect when a sample is present.

The extended polling sequence has one or more extended input pulses. One or more or not any of the extended input pulses may be essentially the same as the regular input pulses. At least one extended input pulse in the extended polling sequence is different than the regular input pulses of the regular polling sequences. The different extended input pulse maybe the last or another extended input pulse in the extended polling sequence. The extended polling sequence may generate one or more volume output signals responsive to the sample volume. A volume output signal may be used to determine whether the sample has sufficient volume for analysis.

When a polling signal is applied to a sample in the biosensor, each pulse of the polling signal typically generates a corresponding output pulse from the sample. One or more output pulses form a polling output signal. Each regular input pulse of the regular polling sequence generates a regular output pulse in a sample output signal. The biosensor detects the presence of the sample when at least one of the regular output pulses reaches a sample threshold, and then applies the extended polling sequence.

Each extended input pulse of the extended polling sequence generates an extended output pulse in a volume output signal. The extended and regular output pulses are essentially the same when the extended and regular input pulses are the same. When an extended input pulse is different than a regular input pulse, the extended output pulse is different than a regular output pulse. The different extended output pulse is responsive to the sample volume in the biosensor, and thus may be used to detect whether the sample has sufficient volume.

One or more volume thresholds may be used to detect when a sample has sufficient or insufficient volume, a volume, a range of volume, a combination thereof, or the like. A sample has sufficient volume when a different extended output pulse reaches a selected volume threshold. A sample has insufficient volume when a different extended output pulse does not reach a volume threshold. A sample has a volume or volume range when the different extended output pulse reaches a volume threshold or reaches one volume threshold but not another volume threshold. Other thresholds may be used including those for other criteria.

FIG. 1 represents a method for assessing a sample volume in a biosensor with an underfill recognition system. In 102, the biosensor is activated. In 104, the biosensor applies a regular polling sequence of a polling signal. In 106, the biosensor detects the presence of the sample. In 108, the biosensor applies an extended polling sequence of the polling signal to the sample. In 110, the biosensor detects whether the sample volume is sufficient for analysis. In 112, the biosensor indicates when the sample volume is insufficient for analysis. In 114, the biosensor applies a test excitation signal when the sample volume is sufficient for analysis. In 116, the biosensor determines the analyte concentration.

In 102 of FIG. 1, the biosensor is activated. The biosensor may be activated by a power switch or button, a sensing mechanism that determines when the biosensor is touched or held by a user, another mechanism that determines when a sensor strip is placed within a measuring device, or the like. When activated, power or more power is supplied and thus starts or increases operation of the electric circuitry in the biosensor. The biosensor initially may run one or more diagnostic routines, obtain the ambient temperature, and/or perform other preparation functions for performing an analysis. The biosensor may delay and/or repeat performance of the preparation functions until a sensor strip is in the measuring device or at another desired time or action. After activation, the biosensor essentially is ready to receive a sample of a biological fluid and to determine the concentration of one or more analytes in the sample.

In 104 of FIG. 1, the biosensor applies a regular polling sequence of a polling signal to the location where a sample of the biological fluid is placed. The location may be a reservoir in a sensor strip or the like. There may be one or more regular polling sequences in a polling signal. FIGS. 2 to 5 each show regular polling sequences of a polling signal. Other regular polling sequences and polling signals may be used.

The regular polling sequence is part of a polling signal. The polling signal is an electrical signal, such as current or potential, that pulses or turns on and off at a set frequency or interval. The polling signal essentially is a sequence of polling pulses separated by polling relaxations. During a polling pulse, the electrical signal is on. On includes time periods when an electrical signal is present. During a polling relaxation, the electrical signal is significantly reduced in amplitude in relation to when the electrical signal is on. Reduced includes when the electrical signal is reduced by at least an order of magnitude in relation to when the electrical signal is on. Reduced also includes when the electrical signal is reduced to off. Off includes time periods when an electrical signal is not present. Off does not include time periods when an electrical signal is present but has essentially no amplitude. The electrical signal may switch between on and off by closing and opening an electrical circuit, respectively. The electrical circuit may be opened and closed mechanically, electrically, or the like. Other on/off mechanisms may be used.

A regular polling sequence is a group of one or more regular input pulse intervals. A regular input pulse interval is the sum of a regular input pulse and a regular relaxation. Each regular input pulse has a regular amplitude and a regular input pulse width. The regular amplitude indicates the intensity of the potential, current, or like of the electrical signal. The regular amplitude may vary or be a constant during the regular input pulse. The regular input pulse width is the time duration of a regular input pulse. The regular input pulse widths in a regular polling sequence may vary or be essentially the same. Each regular relaxation has a regular relaxation width, which is the time duration of a regular relaxation. The regular relaxation widths in a regular polling sequence may vary or be essentially the same.

Regular polling sequences may be selected in response to the redox reaction, one or more analytes, the number and/or configuration of electrodes, one or more mediators, a redox couple, an electrochemical or optical process, a combination thereof, or the like. The selection of regular polling sequences includes the number of pulses, the number and order of similar and different regular input pulses, the regular amplitudes and pulse widths, a combination thereof, or the like. Regular input pulses may be selected to increase or decrease the likelihood of a regular output signal reaching a volume threshold. Likelihood includes the chances or probability of substantially achieving a desired result. Regular polling sequences may be selected in response to other criteria.

The regular polling sequence may have a regular input pulse width of less than about 500 milliseconds (ms) and a regular input pulse interval of less than about 2 seconds (sec). The regular polling sequence may have a regular input pulse width of less than about 100 ms and a regular input pulse interval of less than about 500 ms. The regular polling sequence may have a regular input pulse width in the range of about 0.5 millisecond through about 75 ms and a regular input pulse interval in the range of about 5 ms through about 300 ms. The regular polling sequence may have a regular input pulse width in the range of about 1 millisecond through about 50 ms and a regular input pulse interval in the range of about 10 ms through about 250 ms. The regular polling sequence may have a regular input pulse width of about 5 ms and a regular input pulse interval of about 125 ms. The regular polling sequence may have other pulse widths and pulse intervals.

The biosensor applies the regular polling sequence to the sample during a regular polling period. The regular polling period may be set or selected to be less than about 15 minutes (min), 5 min, 2 min, or 1 min. The regular polling period may be longer. However, the regular polling period actually may be variable because the biosensor may stop the regular polling signal immediately when the presence of a sample is detected, at another time, or another action. After a regular polling period ends and no sample is detected, the biosensor may deactivate, enter a sleep mode, or start another regular polling period. The biosensor may cycle through multiple regular polling periods until a selected number of regular polling periods is completed or a termination event occurs, such as deactivation of the biosensor, the presence of a sample is detected, or the like. The biosensor may enter a sleep mode after a regular polling period or at another selected time or event, where the biosensor nearly deactivates or enters a less active state until further input is obtained.

The regular polling period may be in the range of about 0.5 sec through about 15 min. The regular polling period may be in the range of about 5 sec through about 5 min. The regular polling period may be in the range of about 10 sec through about 2 min. The regular polling period may be in the range of about 20 sec through about 60 sec. The regular polling period may be in the range of about 30 through about 40 sec. The regular polling period may have less than about 200, 100, 50, or 25 pulse intervals. The regular polling period may have from about 2 through about 150 pulse intervals. The regular polling period may have from about 5 through about 50 pulse intervals. The regular polling period may have from about 5 through about 15 pulse intervals. The regular polling period may have about 10 pulse intervals. Other regular polling periods may be used.

In 106 of FIG. 1, the biosensor detects when a sample of a biological fluid is available for analysis. The biosensor detects a sample is present in the biosensor when the sample generates one or more sample output signals in response to the regular polling sequence. The sample may be present in the reservoir of a sensor strip or elsewhere in the biosensor. When the regular polling sequence is applied to the sample, each regular input pulse of the regular polling sequence typically generates a regular output pulse. One or more regular output pulses forms a sample output signal. The biosensor detects the presence of the sample when at least one of the regular output pulses reaches a sample threshold, and then applies the extended polling sequence. The one or more sample output signals are electrical signals, such as current or potential. The biosensor may show the sample output signals on a display and/or may store the sample output signals in a memory device.

A sample output signal indicates a sample is present when one or more regular output pulses in the sample output signal reaches one or more sample thresholds. Reach includes output pulses essentially the same as or greater than a threshold, or output pulses only greater than a threshold. While reach is described in relation to positive orientation, reach may include output pulses essentially the same as or less, or only less, than a threshold when an opposite or negative orientation is used. When no sample is present, the biosensor continues with the regular polling period, cycles through one or more regular polling periods, starts or restarts a regular polling period, deactivates the biosensor, enters a sleep mode, a combination thereof, or the like.

The biosensor detects a sample is present when one or more regular output pulses in the sample output signal reaches one or more sample thresholds. One or more sample thresholds and one or more regular input pulses may be selected to generate a regular output pulse from the sample that is responsive to the presence of a sample. A regular input pulse maybe selected to: (1) generate a regular output pulse that reaches a sample threshold when a sample is present or when the sample is equal to or greater than a selected minimum sample volume; and (2) not generate a regular output pulse that reaches a sample threshold when a sample is not present or when the sample is less than a selected minimum sample volume. A regular input pulse maybe selected to generate a regular output pulse that reaches or does not reach a sample threshold regardless of the sample volume, or regardless of the sample volume equal to or greater than a selected minimum sample volume. Thus, a regular output pulse would be generated when either an underfill condition or a full-fill condition occurs. Other regular input pulses may be selected.

Sample thresholds may be selected to distinguish when a sample is present or not present, when the sample exceeds or does not exceed a selected minimum sample volume, or the like. Sample thresholds may be predetermined threshold values stored in a memory device, obtained from a lookup table, or the like. The predetermined threshold values may have been developed from a statistical analysis of laboratory work. Other predetermined threshold values may be used. Sample thresholds may be measured or calculated threshold values determined in response to the output signals. Other measured or calculated threshold values may be used. Sample thresholds may be selected to identify when one or more output signals are stronger or weaker in response to the sample, the sample volume, or the like.

Sample thresholds may be selected to identify when a change in one or more output signals is responsive to a sample condition. Sample thresholds may be selected by theoretical analysis, a desired precision and/or accuracy of the analysis, or other criteria. A sample threshold may be zero or nearly zero, indicating a sample is present when the sample generates any sample output signal. A sample threshold may be selected to increase or decrease the accuracy and/or precision of detecting when a sample is present. Other sample thresholds may be used.

When the presence of a sample is detected, the biosensor may stop the regular polling sequence immediately, at the end of the regular polling period, or at another selected time. When the presence of a sample is not detected, the biosensor continues to apply the regular polling sequence through one or more regular polling periods. After the one or more regular polling periods are completed and no sample is detected, the biosensor may deactivate, enter a sleep mode, or restart one or more regular polling periods.

The biosensor may start counting the time from when the sample is detected until the test excitation signal is applied or for the duration of the extended pulse sequence. The biosensor may count other time periods. The counting may be part of a buffer to delay further action in response to a slow filling sample. When the biosensor detects the sample is not present, the sample volume is insufficient, or the like, the biosensor may check output pulses from the regular or extended polling signals after one or more delay periods before taking further action. Delay periods may be less than about 3 min, about 2 min, or about 1 minute. Delay periods may be in the range of about 5 sec to about 120 sec, about 10 sec to about 90 sec, about 10 sec to about 60 sec, and about 20 sec to about 45 sec. Other delay periods may be selected. The counting may be used for other criteria, such as to perform other tests, or take other action.

The biosensor also detects when more sample has been added to the reservoir for analysis. In use, the biosensor may restart one or more regular polling periods when a sample has insufficient volume for analysis. The biosensor may request a user to add more sample to the sensor strip. When the additional sample is present in the reservoir of the sensor strip, the larger sample volume also generates one or more sample output signals in response to the regular polling sequence. As discussed, a sample output signal indicates whether additional sample is present or not present when the sample output signal reaches or does not reach, respectively, one or more sample thresholds. When no additional sample is present, the biosensor continues with the regular polling period, cycles through one or more regular polling periods, starts or restarts a regular polling period, deactivates the biosensor, enters a sleep mode, or the like.

The biosensor may use multiple sample thresholds to detect additional sample in the sensor strip. The biosensor may have a first or initial sample threshold to detect the initial presence of a sample in the sensor strip. The biosensor may have a second or refill sample threshold to detect when more sample has been added to the sensor strip, such as after the biosensor requests a user to add more sample. Other multiple sample thresholds may be used.

In 108 of FIG. 1, the biosensor applies an extended polling sequence of a polling signal to the sample of the biological fluid. The biosensor applies the extended polling sequence to the sample after the presence of the sample is detected. The biosensor may apply the extended polling sequence immediately at the end of the regular polling sequence, after a transition period, or at another selected time. Immediately includes little or no time transition from the regular polling sequence to the extended polling sequence. The biosensor may transition from the regular polling sequence to the extended polling sequence without break or interruption. The transition may make the regular polling sequence and part of the extended polling sequence appear to be the same sequence, especially when the regular amplitude of the regular input pulses and the extended amplitude of the initial extended input pulse(s) are essentially the same. There may be one or more extended polling sequences in a polling signal. FIGS. 2 to 5 each show extended polling sequences of a polling signal. Other extended polling sequences and polling signals may be used.

The extended polling sequence is part of the polling signal. The extended polling sequence is a group of one or more extended input pulse intervals. An extended input pulse interval is the sum of an extended input pulse and a extended relaxation. Each extended input pulse has an extended amplitude and a extended input pulse width. The extended amplitude indicates the intensity of the potential, current, or like of the electrical signal. The extended amplitude may vary or be a constant during the extended input pulse. The extended input pulse width is the time duration of an extended input pulse. The extended input pulse widths in a extended polling sequence may vary or be essentially the same. Each extended relaxation has an extended relaxation width, which is the time duration of a extended relaxation. The extended relaxation widths in an extended polling sequence may vary or be essentially the same.

An extended polling sequence may have one or more different extended input pulses and one or more or not any similar extended input pulses. Different extended input pulses are different than the regular input pulses of the regular polling sequence. Similar extended input pulses are essentially the same as the regular input pulses of the regular polling sequence. The last and/or another extended input pulse may be different than the regular input pulses. Extended polling sequences may have one or more higher extended input pulses and one or more lower extended input pulses. Extended polling sequences may have only one different extended input pulse. Extended polling sequences may have only different extended input pulses. Extended polling sequences may have two or more extended input pulses that step-down, step-up, or a combination thereof, which may be all different extended input pulses or a combination of similar and different extended input pulses. Step-down includes extended input pulses where the extended amplitudes decrease with each subsequent input pulse. Step-up includes extended input pulses where the extended amplitudes increase with each subsequent input pulse. The increases and decreases in the extended amplitudes may or may not be the same. Other extended polling sequences may be used.

Extended polling sequences may be selected in response to the redox reaction, one or more analytes, the number and/or configuration of electrodes, one or more mediators, a redox couple, an electrochemical or optical process, a combination thereof, or the like. The selection of extended polling sequences includes the number of pulses or cycles, the number and order of similar and different extended input pulses, the extended amplitudes and pulse widths, a combination thereof, or the like. Extended input pulses may be selected to increase or decrease the likelihood of a volume output signal reaching a volume threshold. Extended polling sequences may be selected in response to other criteria.

Different extended pulses are not the same as regular pulses. Different includes extended pulses with an extended amplitude that is not the same as the regular amplitude(s) of regular pulse(s). Different includes extended pulses having constant amplitude when regular pulse(s) have variable amplitude(s). Different includes extended pulses having variable amplitude when regular pulse(s) have constant amplitude(s). Different includes extended pulses with an extended pulse width that is not the same as the regular pulse width(s) of the regular pulse(s). Other different extended pulses may be used.

The extended polling sequence may be a cycle of extended input pulses. A cycle includes two or more extended input pulses including at least one different extended input pulse. A cycle includes a series of extended polling sequences, which may or may not be the same. A cycle may have one or more similar extended input pulses that are essentially the same as the regular pulses of the regular polling sequence. A cycle may have one or more different extended input pulses, which may or may not be essentially the same as each other. A cycle may have two or more extended input pulses that step-down, step-up, or a combination thereof. Other cycles may be used.

Extended polling sequences may have an extended input pulse width of less than about 500 ms and an extended input pulse interval of less than about 2 sec. Extended polling sequences may have an extended input pulse width of less than about 100 ms and an extended input pulse interval of less than about 500 ms. Extended polling sequence may have an extended input pulse width in the range of about 0.5 millisecond through about 75 ms and an extended input pulse interval in the range of about 5 ms through about 300 ms. Extended polling sequences may have an extended input pulse width in the range of about 1 millisecond through about 50 ms and an extended input pulse interval in the range of about 10 ms through about 250 ms. Extended polling sequences may have an extended input pulse width of about 5 ms and an extended input pulse interval of about 125 ms. Extended polling sequences may have other pulse widths and pulse intervals.

The biosensor applies the extended polling sequence to the sample during an extended polling period. Extended polling periods may be less than about 15 min, 5 min, 2 min, or 1 minute. Extended polling periods may be longer. Extended polling periods may be substantially constant or fixed to improve the detection of the sample volume or sufficiency of the sample volume. Extended polling periods may be selected to act as a buffer for a slow filling sample. Other extended polling periods may used.

After an extended polling period, the biosensor may deactivate, enter a sleep mode, start another extended polling period, start another regular polling period, cycle through multiple regular polling periods when the sample volume is insufficient for analysis, or the like. When the sample volume is sufficient for analysis, the biosensor may apply the test excitation signal immediately after the extended polling period or at other selected time.

Extended polling periods may be in the range of about 0.5 second through about 15 min. Extended polling periods may be in the range of about 5 sec through about 5 min. Extended polling periods may be in the range of about 10 sec through about 2 min. Extended polling periods may be in the range of about 20 sec through about 60 sec. Extended polling periods may be in the range of about 30 sec through about 40 sec. Extended polling periods may have less than about 200, 100, 50, or 25 pulse intervals. Extended polling periods may have from about 2 through about 150 pulse intervals. Extended polling periods may have from about 5 through about 50 pulse intervals. Extended polling periods may have from about 5 through about 15 pulse intervals. Extended polling periods may have about 10 pulse intervals. Other extended polling periods may be used.

In 110 of FIG. 1, the biosensor detects whether the volume of sample is sufficient or not sufficient for analysis of one or more analytes. Sufficient for analysis includes a selected sample volume, a minimum and/or maximum sample volume, one or more ranges of sample volumes, or the like. Sufficient for analysis includes one or more sample volumes selected for a desired accuracy and/or precision of an analyte analysis or other design criteria. Sufficient for analysis includes the absence of a sample essentially too small for any analysis of one or more analytes. Not sufficient or insufficient for analysis includes sample volumes not having one or more of the above or other criteria for sufficient. A biosensor is underfilled or an underfill condition occurs when a sample volume is not sufficient or insufficient for analysis. Underfill condition includes a sample of biological fluid in a biosensor having a size or volume that is not large enough for the biosensor to accurately and/or precisely analyze the concentration of one or more analytes in the biological fluid. The volumes of sample sufficient or insufficient for analysis may be determined experimentally, theoretically, a combination thereof, or the like.

The biosensor detects one or more volume output signals generated by the sample in response to the extended polling sequence. When extended polling sequences are applied to a sample, each extended input pulse of an extended polling sequence generates an extended output pulse. One or more extended output pulses forms a volume output signal. Volume output signals are electrical signals, such as current or potential. Volume output signals may be essentially the same as the sample output signals, except one or more different extended input pulses may generate one or more different extended output pulses. The biosensor may show the volume output signals on a display and/or may store the volume output signals in a memory device.

Volume output signals have similar and extended output pulses. The extended input pulses of an extended polling sequence generate similar extended output pulses or different extended output pulses from a sample. Similar extended output pulses are generated in response to similar extended input pulses. Different extended output pulses are generated in response to different extended input pulses and are responsive to the sample volume in the biosensor. Thus, different extended output pulses may be used to detect the volume of the sample, whether the sample has sufficient volume, a combination thereof, or like criteria.

The biosensor detects if a sample volume is sufficient or insufficient for analysis in response to one or more volume output signals. The biosensor detects if a sample volume is sufficient when one or more different extended output pulses in the volume output signal reaches one or more volume thresholds. The biosensor detects if a sample volume is insufficient when none of the different extended output pulses in the volume output signal reaches one or more volume thresholds. When the biosensor detects a different extended output pulse that indicates the sample volume is insufficient, the biosensor may indicate the sample volume is insufficient, wait for additional sample, restart the extended polling sequence immediately or after a delay period is counted (the delay period may allow full-filling of a slow filling sample), restart the regular polling sequence, enter a sleep mode, deactivate, a combination thereof, or the like. The biosensor may use one or more volume thresholds to determine the sample volume or volume range, whether the sample volume equals, exceeds, and/or is less than one or more volumes, or the like.

The biosensor detects if a sample volume is sufficient or insufficient when one or more different extended output pulses in the volume output signal reaches or does not reach, respectively, one or more volume thresholds. When a sample has less or insufficient volume (an underfill condition), the sample covers less of the electrodes in a sensor strip than a sample with more or sufficient volume (a full-fill condition). Less and more distinguish between insufficient and sufficient sample volume, respectively. Less and more may be selected in response to experimental data, theoretical analysis, a desired precision and/or accuracy of the volume or the analysis, the redox couple or mediator(s) used, the electrode configuration, a combination thereof or the like.

The amount of electrode coverage is related to the sample volume and may affect the extended output pulses generated from the extended input pulses of the extended polling sequence. One or more volume thresholds and one or more different extended input pulses may be selected to generate a different extended output pulse from the sample that is responsive to the sample volume. An extended input pulse may be selected to generate a different extended output pulse that: (1) reaches a volume threshold when the sample covers more of the electrodes, indicating the sample has sufficient or desired volume (full-fill condition); and (2) does not reach a volume threshold when the sample covers less of the electrodes, indicating the sample does not have a sufficient or desired volume (underfill condition). Other different extended output pulses and thresholds may be selected.

Volume thresholds may be selected to distinguish between under-fill and full-fill conditions, different volumes, minimum and/or maximum volumes, volume ranges, particular volumes, a combination thereof, or the like. Volume thresholds may be predetermined threshold values stored in a memory device, obtained from a lookup table, or the like. The predetermined threshold values may have been developed from a statistical analysis of laboratory work. Other predetermined threshold values may be used. Volume thresholds may be measured or calculated threshold values in response to one or more of the output signals. Other measured or calculated threshold values may be used. Volume thresholds may be selected to identify when one or more output signals are stronger or weaker in response to the sample volume. Volume thresholds may be selected to identify when a change in one or more output signals is responsive to a volume condition. Volume thresholds may be selected by theoretical analysis, a desired precision and/or accuracy of the analysis, or other criteria. A volume threshold may be zero or nearly zero, indicating any sample volume is sufficient for analysis. A volume threshold may be essentially the same as the sample threshold. Volume thresholds may be selected to increase or decrease the likelihood of a volume output signal reaching a volume threshold. Likelihood includes the chances or probability of substantially achieving a desired result. Other volume thresholds may be used.

Volume thresholds may be selected to increase or decrease the accuracy and/or precision of the analysis, to detect a sample volume, to detect that a sample volume is insufficient, a combination thereof, or the like. There may be a range or number of volume thresholds that indicate the sample volume or the sample has sufficient volume for analysis. Within this range or number, one or more volume thresholds may be more accurate and/or more precise in indicating the volume or volume sufficiency of the sample than the other volume thresholds. Thus, these more accurate and/or more precise volume thresholds may be selected instead of other volume thresholds that indicate the volume or volume sufficiency of the sample.

The underfill recognition system may use multiple volume thresholds to determine the volume of the sample or the degree of underfill of a biosensor. When a volume output signal exceeds one volume threshold and not another volume threshold, this volume output signal would indicate the sample volume is between the volumes associated with those volume thresholds. More volume thresholds may be used to provide more accurate volume determinations.

Multiple volume thresholds also may be used to determine whether there is sufficient sample volume for multiple or different analyses. When a volume output signal is between two volume thresholds; this volume output signal may indicate there is sufficient sample volume for one analysis but not a second analysis, such as when analyzing for glucose and cholesterol in whole blood. Multiple volume thresholds maybe used to make other determinations responsive to the sample volume.

One or more thresholds may be selected for other design factors. One or more extended input pulses may generate one or more extended polling output pulses responsive to a selected design factor. These output pulses may be used to determine when a design factor is met, and thus whether to start the test excitation signal, restart another regular polling sequence, restart another extended polling sequence, take other action, or the like.

Cycles in an extended polling sequence may be used to create a buffer or delay for a slow filling sample. While the initial extended output pulse(s) in the volume output signal may indicate an insufficient volume, the later or last extended output pulse may indicate a sufficient volume when the sample has substantially finished filling. Cycles in an extended polling sequence may be used for other criteria, such as with or without multiple thresholds to determine the volume or a volume range of a sample.

Regular and extended polling sequences will be generated when the last low extended polling output does not meet the volume threshold value. This cycling may continue indefinitely until the sample volume meets the volume threshold or for a selected number of polling sequences as previously discussed. During this time, additional sample may be added to the sensor strip to trigger meeting the volume threshold. FIG. 2 through FIG. 5 depict the cycling operation.

In 112 of FIG. 1, the biosensor indicates when the sample has insufficient volume for analysis. The biosensor generates one or more error signals or other indicators in response to one or more volume output signals. Indicators on the biosensor or elsewhere may signify that the sample size is not large enough to a user, such as with an icon, flashing light, light-emitting diode, audio sound, text message, or the like. Indictors also may signify that the sample size is not large enough to the biosensor; which may perform some function or action responsive to the insufficient sample size, such as stopping the analysis, restarting the polling signal, deactivating the biosensor, or the like. The biosensor may generate one or more indicators immediately after detection and/or prior to the analysis of the analyte. The biosensor may generate the one or more indicators during or after the analysis of one or more analytes in the sample. The one or more indicators may be shown on a display device and/or retained in a memory device.

The one or more indicators may include a request to the user for the addition of biological fluid to the sample. The request may be an indicator or may be in response to an indicator. The request may be to add sample prior to proceeding with the analysis of the analyte. The biosensor may stop the analyte analysis in response to the one or more indicators and/or in response to the one or more volume output signals indicating that the sample size is not large enough. Stop includes not starting, preventing the start, or suspending the analysis.

The biosensor may request a user to add more sample. The biosensor may request the user for more or less additional sample in response to the sample volume or degree of underfill. For example, a biosensor may request the user to add a larger amount, a double size, or two additional samples to the biosensor, such as when the sample volume is less than half or another selected portion of a desired sample volume. Alternatively, the biosensor may request a user to add a smaller amount, a half size, or other selected portion of additional sample when the sample volume is closer to but not quite a sufficient volume for analysis. One or more volume thresholds may be used to avoid requesting the user to add a third or more additional samples to the biosensor for a single analysis.

In 114 of FIG. 1, the biosensor applies a test excitation signal when sufficient sample volume is available for analysis. The biosensor applies the test excitation signal to the sample when a volume output signal reaches one or more volume thresholds, thus indicating the sample volume is sufficient for analysis, as previously discussed. The test excitation signal may be applied immediately after the extended polling sequence of the polling signal. The test excitation signal may be applied within a selected time period after the extended polling sequence of the polling signal. The test excitation signal may be stopped from being applied until a volume output signal indicates a sufficient sample is available for analysis. The test excitation signal may initiate and/or may be part of an electrochemical, optical, or like analysis of the analyte concentration in the sample.

The test excitation signal is an electrical signal, such as current or potential, that pulses or turns on and off at a set frequency or interval. FIGS. 2 to 5 each show a test excitation signal, which is an assay potential sequence of a gated amperometry electrochemical analysis. Other test excitation signals may be used. The sample generates a test output signal in response to the test excitation signal. The test output signal is an electrical signal, such as current or potential, which may be used to determine one or more analyte concentrations in the sample.

The test excitation signal is a sequence of test pulses separated by test relaxations. During a test pulse, the electrical signal is on. On includes time periods when an electrical signal is present. During a test relaxation, the electrical signal is significantly reduced in amplitude in relation to when the electrical signal is on. Reduced includes when the electrical signal is reduced by at least an order of magnitude in relation to when the electrical signal is on. Reduced also includes when the electrical signal is reduced to off. Off includes time periods when an electrical signal is not present. Off does not include time periods when an electrical signal is present but has essentially no amplitude. The electrical signal may switch between on and off by closing and opening an electrical circuit, respectively. The electrical circuit may be opened and closed mechanically, electrically, or the like. Other on/off mechanisms may be used.

A test excitation signal may have one or more test pulse intervals. A test pulse interval is the sum of a test pulse and a test relaxation. Each test pulse has a test amplitude and a test pulse width. Each test pulse may have the same or different test amplitudes and/or the same or different test pulse widths. The test amplitude indicates the intensity of the potential, the current, or the like of the electrical signal. The test amplitude may vary or be a constant during the test pulse. The test pulse width is the time duration of a test pulse. The test pulse widths in a test excitation signal may vary or be essentially the same. Each test relaxation has a test relaxation width, which is the time duration of a test relaxation. The test relaxation widths in a test excitation signal may vary or be essentially the same.

The test excitation signal may have a test pulse width of less than about 5 sec and a test pulse interval of less than about 15 sec. The test excitation signal may have a test pulse width of less than about 3, 2, 1.5, or 1 sec and a test pulse interval of less than about 13, 7, 4, 3, 2.5, or 1.5 sec. The test excitation signal may have a test pulse width in the range of about 0.1 sec through about 3 sec and a test pulse interval in the range of about 0.2 second through about 6 sec. The test excitation signal may have a test pulse width in the range of about 0.1 second through about 2 sec and a test pulse interval in the range of about 0.2 second through about 4 sec. The test excitation signal may have a test pulse width in the range of about 0.1 second through about 1.5 sec and a test pulse interval in the range of about 0.2 second through about 3.5 sec. The test excitation signal may have a test pulse width in the range of about 0.4 second through about 1.2 sec and a test pulse interval in the range of about 0.6 second through about 3.7 sec. The test excitation signal may have a test pulse width in the range of about 0.5 second through about 1.5 sec and a test pulse interval in the range of about 0.75 second through about 2 sec. The test excitation signal may have a test pulse width of about 1 second and a test pulse interval of about 1.5 sec. The test excitation signal may have other pulse widths and pulse intervals.

The biosensor applies the test excitation signal to the sample during a test period. The test period may have the same or a different duration than the polling period or either of the regular and extended polling sequences. The test excitation signal may be part of or in addition to an electrochemical or optical analysis system.

The test period of the test excitation signal may be less than about 180, 120, 90, 60, 30, 15, 10, or 5 sec. The test period may be in the range of about 1 second through about 100 sec. The test period may be in the range of about 1 second through about 25 sec. The test period may be in the range of about 1 second through about 10 sec. The test period may be in the range of about 2 sec through about 3 sec. The test period may be about 2.5 sec. The test period may have less than about 50, 25, 20, 15, 10, 8, 6, or 4 test pulse intervals. The test period may have test pulse intervals in the range of about 2 through about 50. The test period may have test pulse intervals in the range of about 2 through about 25. The test period may have test pulse intervals in the range of about 2 through about 15. The test period may have about 10 test pulse intervals. Other test periods may be used.

In 116 of FIG. 1, the biosensor determines the analyte concentration of the sample from a test output signal. The polling and test excitation signals may be part of or an addition to an electrochemical or optical sensor system used to determine one or more analyte concentrations in a sample of biological fluid. The sample generates one or more test output signals in response to the test excitation signal. The biosensor measures the test output signals generated by the sample. The biosensor may show the test output signals on a display and/or may store the test output signal in a memory device. The biosensor correlates the test output signals to the concentration of the analyte in the sample.

In electrochemical and optical sensor systems, an oxidation/reduction or redox reaction of an analyte in the sample generates one or more assay or test output signals. A Redox reaction is a chemical reaction between two species involving the transfer of at least one electron from a first species to a second species. A redox reaction includes oxidation and reduction half-cells. The oxidation half-cell of the reaction involves the loss of at least one electron by the first species. The reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained. An enzyme or similar species may be added to the sample to enhance the specificity of the redox reaction.

Optical sensor systems generally measure the amount of light absorbed or generated by the reaction of a chemical indicator with the analyte redox reaction. An enzyme may be included with the chemical indicator to enhance the reaction kinetics. The test excitation signal initiates the analysis by the optical sensor system. The test output signal or light from an optical system may be converted into an electrical signal such as current or potential, which is used to determine the analyte concentration.

In light-absorption optical systems, the chemical indicator produces a reaction product that absorbs light. An incident excitation beam from a light source is directed toward the sample. The incident beam may be reflected back from or transmitted through the sample to a detector. The detector collects and measures the attenuated incident beam (test output signal). The amount of light attenuated by the reaction product is an indication of the analyte concentration in the sample.

In light-generated optical systems, the chemical detector fluoresces or emits light in response to the analyte redox reaction. A detector collects and measures the generated light (test output signal). The amount of light produced by the chemical indicator is an indication of the analyte concentration in the sample.

In electrochemical sensor systems, the test excitation signal initiates the redox reaction of the analyte in the sample of the biological fluid. The test excitation signal may be a potential or current and may be constant, variable, or a combination thereof such as when an AC signal is applied with a DC signal offset. The test excitation signal may be applied as a single pulse or in multiple pulses, sequences, or cycles. An enzyme or similar species may be used to enhance the redox reaction of the analyte. A mediator may be used to maintain the oxidation state of the enzyme. A mediator is a substance that may be oxidized or reduced and that may transfer one or more electrons. A mediator is a reagent and is not the analyte of interest, but provides for the indirect measurement of the analyte. More simply, the mediator undergoes a redox reaction in response to the oxidation or reduction of the analyte. The oxidized or reduced mediator then undergoes the opposite reaction at the working electrode of the sensor strip and is regenerated to its original oxidation number. The redox reaction generates a test output signal that may be measured constantly or periodically during transient and/or steady-state output. Various electrochemical processes may be used such as amperometry, coulometry, voltammetry, gated amperometry, gated voltammetry, and the like.

In amperometry, a potential or voltage is applied to a sample of the biological fluid. The redox reaction of the analyte generates a current in response to the potential. The current is measured at a fixed time at a constant potential to quantify the analyte in the sample. Amperometry generally measures the rate at which the analyte is oxidized or reduced to determine the analyte concentration in the sample. Biosensor systems using amperometry are described in U.S. Pat. Nos. 5,620,579; 5,653,863; 6,153,069; and 6,413,411.

In coulometry, a potential is applied to a sample of the biological fluid to exhaustively oxidize or reduce the analyte within the sample. The potential generates a current that is integrated over the time of oxidation/reduction to produce an electrical charge representing the analyte concentration. Coulometry generally captures the total amount of analyte within the sample, necessitating knowledge of sample volume. A biosensor system using coulometry for whole blood glucose measurement is described in U.S. Pat. No. 6,120,676.

In voltammetry, a varying potential is applied to a sample of biological fluid. The redox reaction of the analyte generates current in response to the applied potential. The current is measured as a function of applied potential to quantify the analyte in the sample. Voltammetry generally measures the rate at which the analyte is oxidized or reduced to determine the analyte concentration in the sample.

In gated amperometry and gated voltammetry, pulsed excitations may be used as described in U.S. Pat. Pubs. 2008/0173552, filed Dec. 19, 2007, and 2008/0179197, filed Feb. 26, 2006, respectively.

The test excitation and output signals may be added to or incorporated with the pulsed excitation and output signals of an electrochemical sensor system. The test excitation signal may be part of the test excitation signal applied to a sample in gated amperometry or gated voltammetry systems. The test excitation signal may be the portion of the test excitation signal that is applied to the sample during the test period. The test output signal may be the portion of the test output signal generated by a sample during the test period. The test excitation and output signals may be added to or incorporated with other electrochemical sensor systems.

In a biosensor with an underfill recognition system, the regular and extended amplitudes of the polling sequences may be selected to reduce or substantially eliminate any irreversible alteration of the analyte concentration(s) in the sample during application of the polling signal. "Irreversible alteration" is a change in mass, volume, chemical or electrical properties, a combination thereof, or the like from an original condition to another condition that cannot be undone or essentially returned to the original condition. One or more larger regular or extended amplitudes in the polling signal may irreversibly alter the analyte concentrations in the sample. Larger amplitudes or longer pulse widths irreversibly oxidize, reduce, or otherwise alter the analyte(s) in the sample. Smaller amplitudes or shorter pulse widths do not irreversibly oxidize, reduce, or otherwise alter the analyte(s) in the sample. In analyses that correlate the analyte concentration to the diffusion rate of the redox reaction, the original diffusion rate cannot be obtained once part of the analyte is irreversibly altered by the pulse with a larger amplitude or longer pulse width. In these analyses, the pulse width is more likely to alter the analyte concentration.

In a biosensor using gated amperometry with an underfill recognition system, one or more large pulses in the polling signal may oxidize or alter part of the analyte(s) in the sample, such as glucose in whole blood. The regular and extended amplitudes of the polling sequences may be small, such as less than about 1.5 volts (V), 1.0 V, 800 millivolts (mV), 600 mV, or 500 mV. The regular and extended amplitudes may be in the range of about 5 mV to about 800 mV, about 25 mV to about 600 mV, or about 50 mV to about 500 mV. The regular amplitude may be in the range of about 300 mV to about 800 mV, about 350 mV to about 600 mV, or about 400 mV to about 500 mV. The extended amplitude may be in the range of about 5 mV to about 350 mV, about 10 mV to about 250 mV, about 25 mV to about 150 mV, or about 50 mV to about 100 mV. Other biosensors may be used including those with other electrochemical and optical analyses.

In a biosensor using gated amperometry with an underfill recognition system, one or more long pulse widths in the polling signal may oxidize or alter part of the analyte(s) in the sample, such as glucose in whole blood. The pulse widths of the regular and extended poling sequences may be short, such as at most 50 ms or at most 20 ms. The regular and extended pulse widths may be in the range of about 1 ms to about 15 ms or about 5 ms to about 10 ms. Other biosensors may be used including those with other electrochemical and optical analyses.

In a biosensor using gated amperometry with an underfill recognition system, the polling output signals may have a current less than about 1,500 nanoamps (nA), 1,000 nA, or 500 nA. The polling output signals are generated in response to the polling signals, which include regular and extended polling sequences. Polling output signals include sample and volume output signals. Sample output signals are generated in response to regular polling sequences. Volume output signals are generated in response to extended polling sequences. The sample output signals may have a current in the range of about 5 nA to about 800 nA, about 50 nA to about 500 nA, about 100 nA to about 400 nA, or about 200 nA to about 300 nA. The volume output signals may have a current in the range of about 5 nA to about 800 nA, about 50 nA to about 500 nA, about 100 nA to about 400 nA, or about 200 nA to about 300 nA. Other biosensors may be used including those with other electrochemical and optical analyses.

FIGS. 2 to 5 are graphs illustrating the polling and test excitation signals used in a biosensor with an underfill recognition system. The polling signals have regular and extended polling sequences. The polling and test excitation signals are part of a gated amperometry electrochemical analysis, thus the test excitation signals are assay potential sequences. Other polling and test excitation signals may be used, including those used with other electrochemical and optical analyses of an analytes in biological fluids and polling signals that precede a coulometric or voltammetric test excitation signal.

Figure 2:
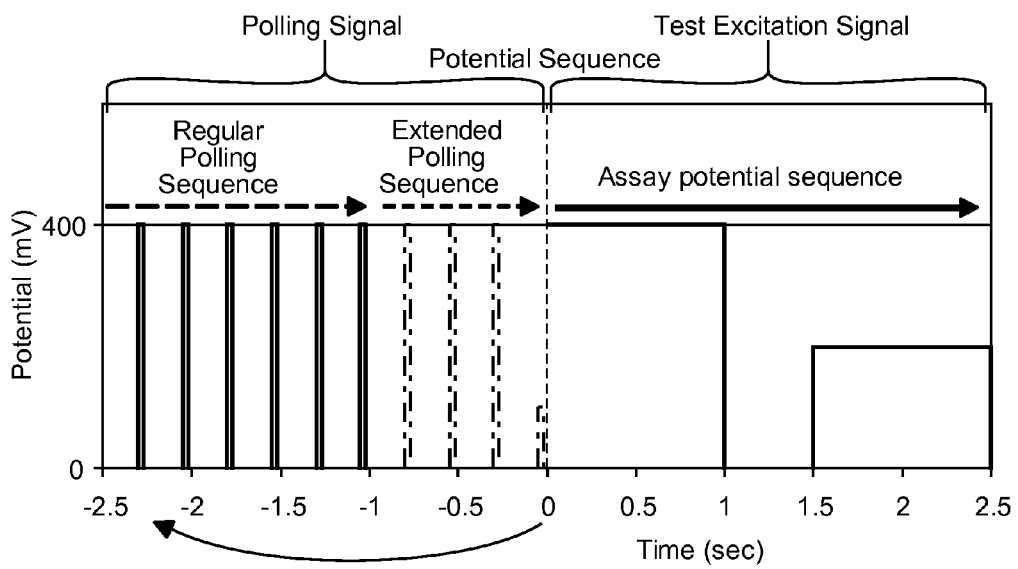
FIG. 2 is a graph illustrating the regular and extended polling sequences of a polling signal and a test excitation signal in a biosensor with an underfill recognition system.

In FIG. 2, the polling signal has a regular polling sequence of six regular input pulses and an extended polling sequence of four extended input pulses. The regular input pulses have a regular amplitude of about 400 mV. The extended polling sequence has three similar extended input pulses followed by one different extended input pulse. The three similar extended input pulses have an extended amplitude of about 400 mV. The different extended input pulse is the last extended input pulse and has an extended amplitude of about 100 mV. The pulse widths and relaxation widths of the regular and extended polling signals are essentially the same. The reverse arrow illustrates that the regular polling sequence and/or the extended polling sequence may restart, if desired, such as when no sample is present, the sample has insufficient volume, or other criteria.

The assay potential sequence in FIG. 2 has two assay pulses with an assay pulse width of about 1 sec and a relaxation width of about 0.5 sec. The first assay pulse has an assay pulse potential of about 400 mV, which is essentially the same as the regular amplitudes of the regular input pulses of the regular polling sequence and the extended amplitudes of the similar extended input pulses of the extended polling sequence. The second assay pulse has an assay pulse potential of about 200 mV. The first assay pulse starts essentially at the end of the last extended input pulse in the extended polling sequence.

Figure 3:
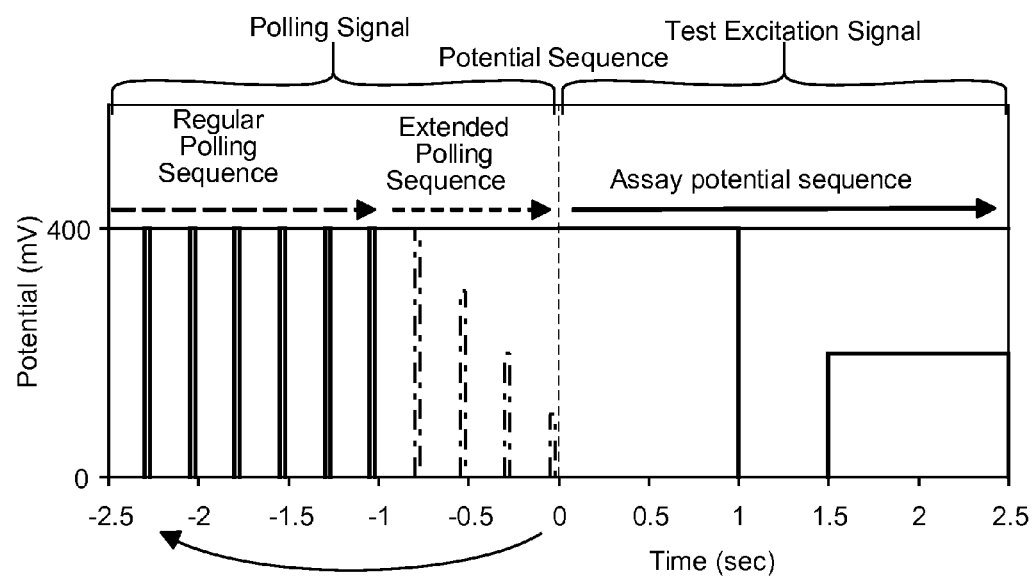
FIG. 3 is a graph illustrating the regular and extended polling sequences of another polling signal with the test excitation signal used in FIG. 2.

In FIG. 3, the polling signal has a regular polling sequence of six regular input pulses and an extended polling sequence of four extended input pulses. The regular input pulses have a regular amplitude of about 400 mV. The extended polling sequence has one similar extended input pulse followed by three different extended input pulses. The similar extended input pulse has an extended amplitude of about 400 mV, which is essentially the same as the regular amplitudes of the regular input pulses. The different extended input pulses step-down or have decreasing extended amplitudes of about 300 mV, about 200 mV, and about 100 mV, which are different than the regular amplitudes of the regular input pulses. The pulse widths and relaxation widths of the regular and extended polling signals are essentially the same. The reverse arrow illustrates that the regular polling sequence and/or the extended polling sequence may restart, if desired, such as when no sample is present, the sample has insufficient volume, or another criteria. The assay potential sequence in FIG. 3 is substantially the same as in FIG. 2.

Figure 4:
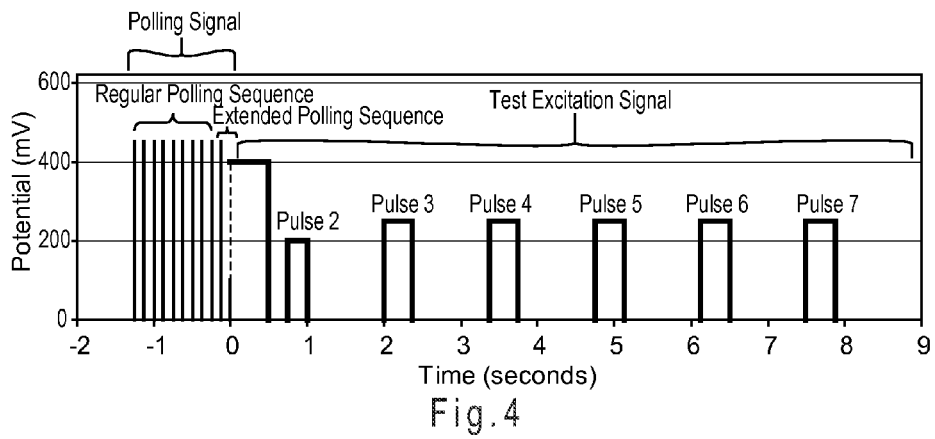
FIG. 4 is a graph illustrating the regular and extended polling sequences of an additional polling signal and an additional test excitation signal in a biosensor with an underfill recognition system.

In FIG. 4, the polling signal has a regular polling sequence of nine regular input pulses and an extended polling sequence of two extended input pulses. The regular input pulses have a regular amplitude of about 450 mV. The extended polling sequence has one similar extended input pulse followed by one different extended input pulse. The similar extended input pulse has an extended amplitude of about 450 mV, which is essentially the same as the regular amplitudes of the regular input pulses. The different extended input pulse has an extended amplitude of about 100 mV, which is different than the regular amplitudes of the regular input pulses. The pulse widths and relaxation widths of the regular and extended polling signals are essentially the same. While no reverse arrow is illustrated, the regular polling sequence and/or the extended polling sequence may restart if desired, such as when no sample is present, the sample had insufficient volume, or another criteria.

The assay potential sequence in FIG. 4 has seven assay pulses having various pulse widths from about 0.25 sec to about 0.5 sec and various relaxation widths from about 0.25 sec to about 1 sec. The first assay pulse has an assay pulse potential of about 400 mV. The second assay pulse has an assay pulse potential of about 200 mV. The third through the seventh assay pulses each have an assay pulse potential of about 250 mV. The first assay pulse starts essentially at the end of the last extended input pulse in the extended polling sequence.

Figure 5A:
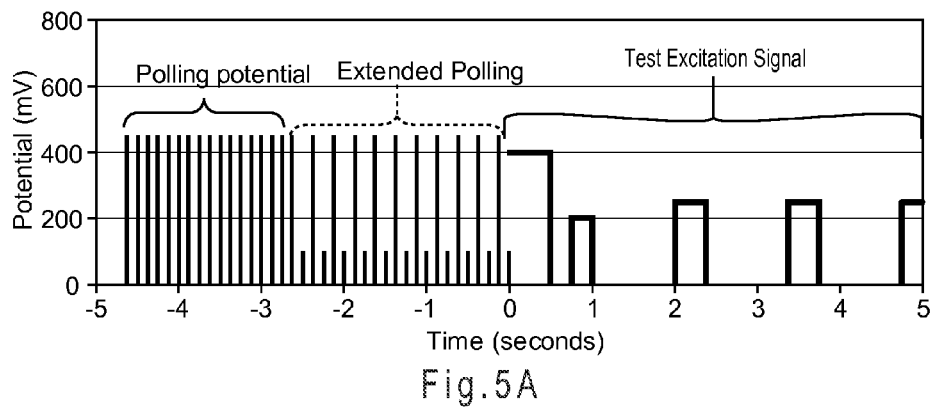
FIG. 5A is a graph illustrating the regular and extended polling sequences of a cyclical polling signal and a test excitation signal in a biosensor with an underfill recognition system.
Figure 5B:
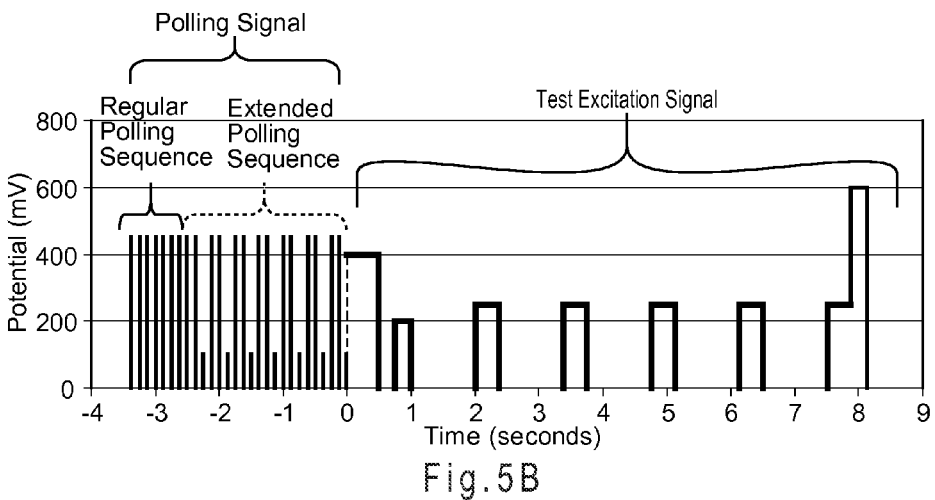
FIG. 5B is a graph illustrating the regular and extended polling sequences of another cyclical polling signal and another test excitation signal in a biosensor with an underfill recognition system.

In FIG. 5A and FIG. 5B, the extended polling sequences have multiple cycles of extended input pulses with higher and lower extended amplitudes. In FIG. 5A, the extended polling sequence has two-pulse cycles, which include one higher pulse and one lower pulse. In FIG. 5B, the extended polling sequence has three-pulse cycles, which include two higher pulses and one lower pulse.

In FIG. 5A, the polling signal has a regular polling sequence of sixteen regular input pulses and an extended polling sequence of twenty-two extended input pulses. The regular input pulses have a regular amplitude of about 450 mV. The extended polling sequence has eleven cycles, each with a start cycle pulse and an end cycle pulse. The start cycle pulse is a similar extended input pulse with an extended amplitude of about 450 mV, which is essentially the same as the regular amplitudes of the regular input pulses. The end cycle pulse is a different extended input pulse with an extended amplitude of about 100 mV, which is different than the regular amplitudes of the regular input pulses. The pulse widths and relaxation widths of the regular and extended polling signals are essentially the same. While there is no reverse arrow illustrated, the regular polling sequence and/or the extended polling sequence may restart, if desired, such as when no sample is present, the sample has insufficient volume, or another criteria. While FIG. 5A illustrates a regular polling sequence followed by an extended polling sequence with eleven cycles, the regular polling sequence may be implemented after each cycle or after multiple cycles of the extended polling sequence.

The assay potential sequence has five assay pulses having various pulse widths from about 0.25 sec to about 0.5 sec and various relaxation widths from about 0.25 sec to about 1 sec. The first assay pulse has an assay pulse potential of about 400 mV. The second assay pulse has an assay pulse potential of about 200 mV. The third through the fifth assay pulses each have an assay pulse potential of about 250 mV. The first assay pulse starts essentially at the end of the last extended input pulse in the extended polling sequence.

In FIG. 5B, the polling signal has a regular polling sequence of seven regular input pulses and an extended polling sequence of twenty-one extended input pulses. The regular input pulses have a regular amplitude of about 450 mV. The extended polling sequence has seven cycles, each with a start cycle pulse, a middle cycle pulse, and an end cycle pulse. The start and middle cycle pulses are similar extended input pulses with an extended amplitude of about 450 mV, which is essentially the same as the regular amplitude of the regular input pulses. The end cycle pulse is a different extended input pulse with an extended amplitude of about 100 mV, which is different than the regular amplitudes of the regular input pulses. The pulse widths and relaxation widths of the regular and extended polling signals are essentially the same. While there is no reverse arrow illustrated, the regular polling sequence and/or the extended polling sequence may restart, if desired, such as when no sample is present, the sample has insufficient volume, or another criteria. While FIG. 5B illustrates a regular polling sequence followed by an extended polling sequence with seven cycles, the regular polling sequence may be implemented after each cycle or after multiple cycles of the extended polling sequence.

The assay potential sequence has seven assay pulses having various pulse widths from about 0.25 sec to about 0.5 sec and various relaxation widths from about 0.25 sec to about 1 sec. The first assay pulse has an assay pulse potential of about 400 mV. The second assay pulse has an assay pulse potential of about 200 mV. The third through the sixth assay pulses each have an assay pulse potential of about 250 mV. The seventh assay pulse has an assay pulse potential that varies from about 250 mV to about 600 mV. The first assay pulse starts essentially at the end of the last extended input pulse in the extended polling sequence.

In FIG. 2 through FIG. 5, the regular polling sequences have multiple regular input pulses that are essentially the same. A sample generates a regular output pulse in response to each regular input pulse. The presence of a sample is detected when a regular output pulse reaches a sample threshold as previously discussed. When no regular output pulse reaches a sample threshold, the regular polling sequence restarts and/or other actions are taken. When the presence of a sample is detected, the extended polling sequence is applied.

Each extended polling sequence in FIG. 2 through FIG. 5 has at least one similar extended input pulse and at least one different extended input pulse. A sample generates similar and different extended output pulses in response to these extended polling sequences. The sample has sufficient or insufficient volume when a different extended output pulse reaches or does not reach, respectively, a volume threshold. When the sample has sufficient volume, the test excitation signal is applied.

The different extended input pulses in the extended polling sequences of FIG. 2 through FIG. 5 generate different extended output pulses from a sample. In FIG. 2 and FIG. 4, only the last input pulse in the extended polling sequence is a different extended input pulse. Thus, a volume output signal from the extended polling sequence of FIG. 2 would have three similar extended output pulses followed by one different extended output pulse. In contrast, a volume output signal from FIG. 4 would have one similar extended output pulse followed by one different extended output pulse.

In FIG. 3, the last three input pulses in the extended polling sequence are different extended input pulses. In these three different extended input pulses, the extended amplitudes decrease or step-down with each subsequent pulse. A volume output signal from the extended polling sequence of FIG. 3 would have one similar extended output pulse followed by three different extended output pulses, each having step-down amplitudes. A sample volume or range of sample volumes may be determined when one or more volume thresholds are used with the extended polling sequence of FIG. 3.

In FIG. 5A and FIG. 5B, the extended polling sequences are cycles of similar and different extended input pulses. A sample generates cyclical volume output signals in response to the cyclical extended polling sequences. Each cycle in the volume output signal from the extended polling sequence of FIG. 5A would have one similar extended output pulse followed by one different extended output pulse. Each cycle in the volume output signal from the extended polling sequence of FIG. 5B would have two similar extended output pulses followed by one different extended output pulse. The cycles may create a buffer for a slow filling sample, determine a volume or volume range of a sample, a combination thereof, or the like.

While conventional underfill detection systems identify underfill conditions, these underfill detection systems typically reject a glucose measurement when there is an underfill condition, and thus require a new analysis using a new sensor strip. In contrast, the underfill recognition system can request a user to add more sample to the sensor strip when there is an underfill condition. The analysis may be performed using the same sensor strip. Thus, the underfill recognition system may reduce the number of sensor strips and related costs associated with underfill conditions. The underfill recognition system has other advantages in comparison to underfill detection systems such as improving the precision and/or accuracy of the analysis, the volume assessment, or the like in a biosensor.

Figure 6:
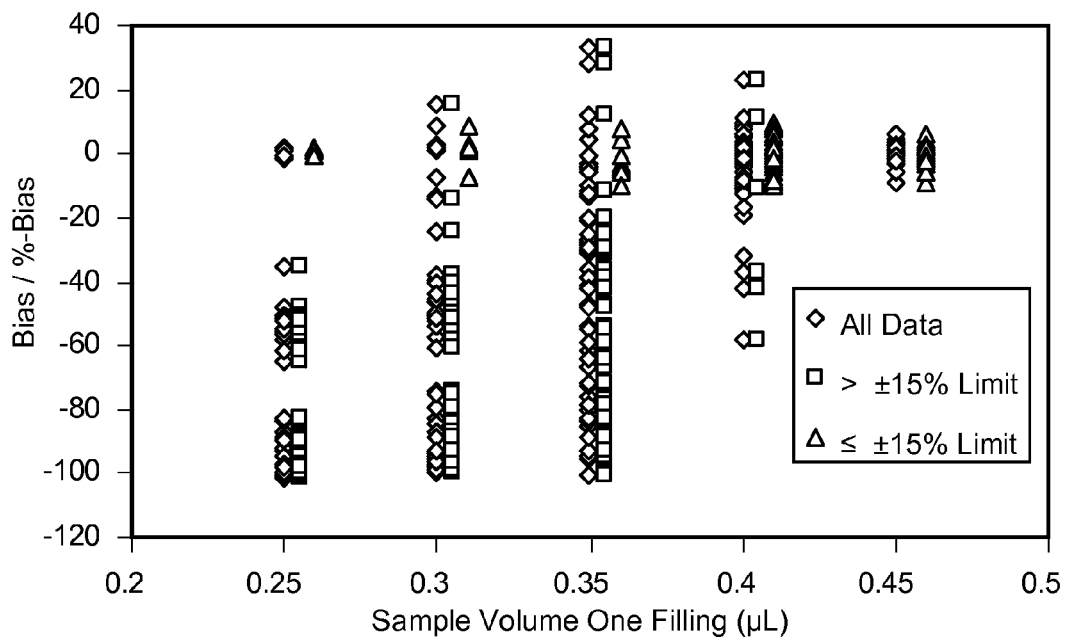
FIG. 6 illustrates the results of a sample volume study for conventional underfill detection systems.
Figure 7:
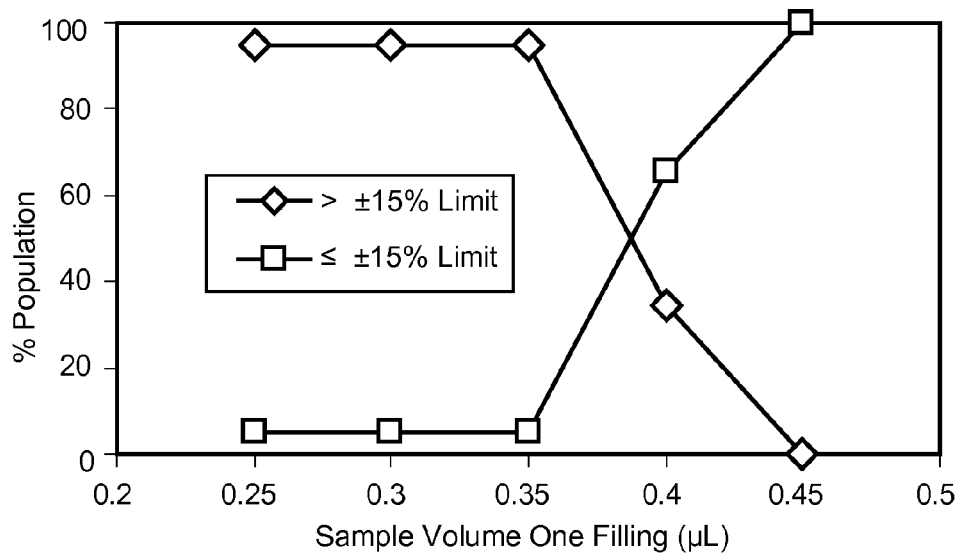
FIG. 7 illustrates the %-Population of glucose readings for the sample volume study of FIG. 6.
Figure 8:
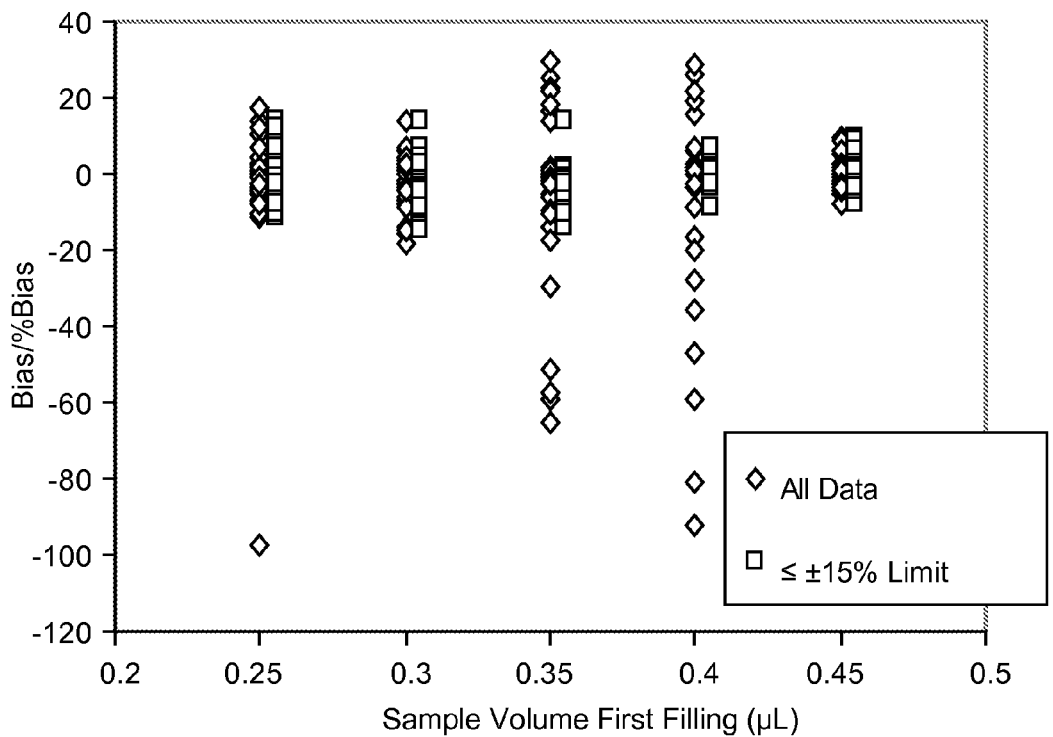
FIG. 8 illustrates the results of a sample volume study for the underfill recognition system.

FIG. 6 through FIG. 9 depict comparisons between conventional underfill detection systems and the underfill recognition system. FIG. 6 and FIG. 8 plot the absolute bias or percent bias (Bias/%-Bias) of glucose readings in relation to sample volume. Bias may be expressed in terms of "absolute bias" or "percent bias". Absolute bias may be expressed in the units of the measurement, such as mg/dL, while percent bias may be expressed as a percentage of the absolute bias value over the reference value. In this volume study, the reference analyte concentration values were obtained from full-filled sensor strips. The Bias/%-Bias relationship represents the inaccuracy of the glucose reading or measurement from the biosensor for a sample with a known or standard glucose concentration that was fully filled. In FIG. 6 through FIG. 9, when Bias/%-Bias exceeded a >±15% limit, the analysis was determined to be in error. When the Bias/%-Bias was less than or equal to the ±15% limit, the analysis was determined to have no error in the glucose concentration determination.

FIG. 6 illustrates the results of a sample volume study performed by filling multiple sensor strips with whole blood sample volumes ranging from 0.2 to 0.45 µL. Thus, the data in FIG. 6 indicated the errors in glucose measurements associated with volumes smaller than the functional volume, which in this volume study was 0.45 µL. The functional volume is the sample volume that will result in 95% or more of the glucose readings having a bias within a specified limit, which in this volume study was ≤±15%.

Each analysis, corresponding to a single sensor strip, is represented with a diamond. Of the total analyses represented by diamonds, those that were within the ±15% limit also are represented by triangles. Of the total analyses represented by diamonds, those that were determined as being underfilled using a conventional method also are represented by squares. Using the conventional system, the analyses represented by the squares would have reported an analysis error, necessitating a new strip and sample. Fill sample volumes of less than about 0.45 µL resulted in fewer and fewer analyses falling within the ±15% limit. The majority of negative biases correspond to the underfilled volumes of 0.25 µL to 0.35 µL. Thus, a major source of error may be attributed to underfilling the biosensors.

FIG. 7 depicts two plots of the %-Population of glucose readings from the sample volume study of FIG. 6 in relation to sample volume. The first plot shows the percentage of the population of the glucose measurements where errors are detected, such as when the Bias/%-Bias exceeds the ±15% limit. The second plot shows the percentage of population of the glucose measurements where no errors are detected, such as when the Bias/%-Bias does not exceed the ±15% limit. The first plot of detected errors is essentially a mirror image or opposite of the second plot of no detected errors. As the sample volume decreases from 0.45 μL, the number of glucose readings within the ±15% limit decreased from about 100% to about 5% at 0.35 μL and smaller sample volumes. Conversely, as the sample volume decreases from 0.45 μL, the number of underfilled sensors increased from about 0% to about 95% at 0.35 μL and smaller sample volumes. For fill sample volumes from 0.2 μL to about 0.35 μL, only about 5% of the analyses fell within the ±15% limit in this particular volume study. Thus, for fill volumes of about 0.35 μL and below, 95% of the analyses would have to be repeated with a new sensor strip.

FIG. 8 depicts a plot of the Bias/%-Bias of glucose readings in relation to sample volume from a volume study of biosensors having an underfill recognition system, which were intentionally underfilled by a first filling and subsequently filled with a second filling in response to the method of FIG. 1. The sample volume shown in FIG. 8 is the sample volume of the first filling. Of all the analyses (represented by diamonds), most also are represented by squares, showing that the analysis fell within the ±15% limit after underfill was recognized by the method of FIG. 1 and additional sample was added. Thus, the data in FIG. 8 indicate that errors in glucose measurements associated with smaller sample volumes on the first filling are reduced or substantially eliminated with additional sample added in response to the method of FIG. 1. A majority of the Bias/%-Bias values are within the ±15% limit, especially in the first fill sample volume range of 0.25 μL to 0.35 μL. Those outside the limit may be identified by additional testing using the underfill recognition system. Thus, a major source of error attributed to underfilling the biosensors may be reduced or substantially eliminated by a second filling of a biosensor in response to the underfill recognition system.

Figure 9:
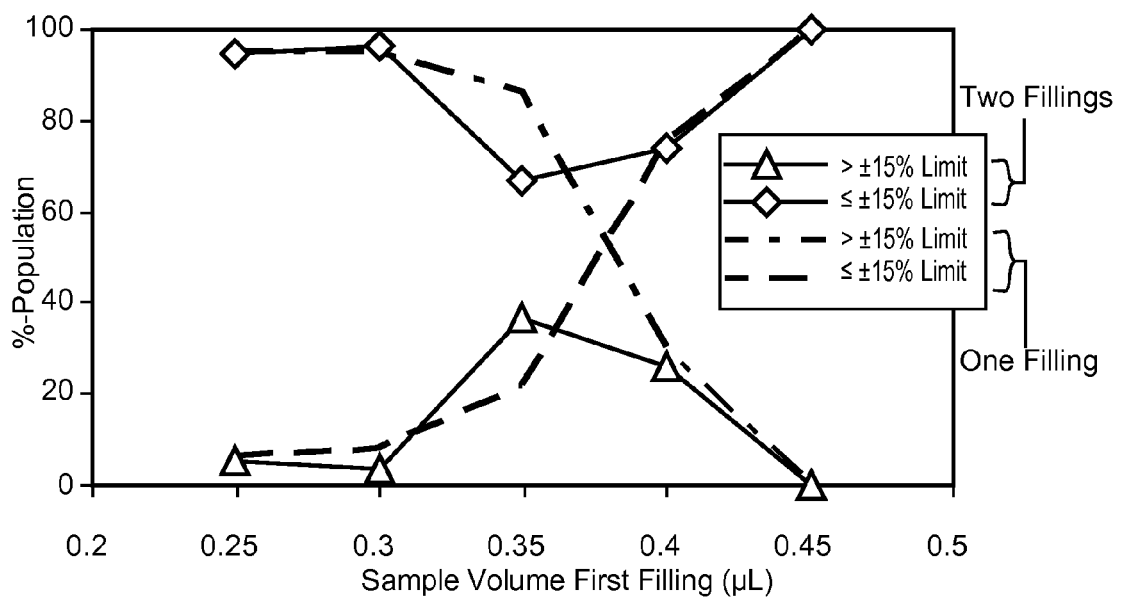
FIG. 9 illustrates the %-Population of glucose readings for the sample volume study of FIG. 8.

FIG. 9 depicts an overlay of two plot sets of the %-Population of glucose readings from the sample volume study of FIG. 8 in relation to sample volume. Each plot set contains two plots. The first plot set (dash lines) shows the Bias/%-Bias of glucose readings in relation to sample volume for biosensors intentionally underfilled by a first filling. The second plot set (solid lines) shows the Bias/%-Bias of glucose readings in relation to sample volume for biosensors intentionally underfilled by a first filling and subsequently filled with a second filling. Each plot set has two plots, which show the percentage of population of the glucose analyses where underfill errors are detected and are not detected, such as when the Bias/%-Bias exceeds or does not exceed the ±15% limit.

The first plot set in FIG. 9 (dash lines) shows the Bias/%-Bias for biosensors after a first filling. As the sample volume decreases from 0.45 μL, the number of glucose readings falling within the ±15% limit decreases from about 100% to about 20% at 0.35 μL and then decrease to about 5% at 0.25 μL. Conversely, as the sample volume decreases from 0.45 μL, the number of glucose readings falling outside of the ±15% limit increases from about 0% to about 80% at 0.35 μL and then increases to about 95% at 0.25 μL.

The second plot set in FIG. 9 (solid lines) shows the Bias/%-Bias for biosensors intentionally underfilled by a first filling and subsequently filled with a second filling in response to the underfill recognition method of FIG. 1. As the sample volume decreases from 0.45 μL, the number of glucose readings outside of the ±15% limit increases from about 0% to about 35% at 0.35 μL. However instead of following the trend of the first plot set, where the number of glucose readings outside of the ±15% limit continues to increase, the trend is reversed and the number of glucose readings outside of the ±15% limit decreases to about 5% at 0.25 μL. Additionally, as the sample volume decreases from 0.45 μL, the number of glucose readings falling within the ±15% limit initially decreases from about 100% to about 65% at 0.35 μL and then increases to about 95% at 0.25 μL. The difference or gap between the number of glucose readings outside of the ±15% limit with no second filling and in biosensors having a second filling in response to the method of FIG. 1 represents the potential savings from reducing the number of wasted sensor strips due to insufficient sample volume for analysis.

The underfill recognition system may be implemented on a biosensor that applies the polling and test excitation signals to a sample in a sensor strip. The sensor strip may have various configurations including those with multiple electrodes and conductors. The sensor strip may have 2, 3, 4, or more electrodes. The sensor strip may have one or more working electrodes, one or more counter electrodes, one or more other electrodes, a combination thereof, or the like. The sensor strip may have 2, 3, 4, or more conductors. The sensor strip may have at least one counter electrode, at least one working electrode, and at least one trigger electrode, which may be a separate electrode or a sub-element of the counter electrode. A sensor strip with working, counter, and trigger electrodes is described in U.S. Pat. No. 6,531,040. Other biosensors may be used including those with additional electrodes and different configurations.

The underfill recognition system may be implemented on a biosensor using a sensor strip with a selected configuration, composition, or other properties. The sensor strip may have a selected electrode pattern, electrode composition or properties, mediator system, redox couple, combination thereof, or the like. The sensor strip may be used with selected regular polling sequences, extended polling sequences, test excitation signals, a combination thereof, or the like. The sensor strip properties may be select to improve one or more of the polling output signals, which includes the sample and volume output signals. Improves includes having a more detectable polling output signal. Detectable includes having a stronger and/or more distinct polling output signal. Improves includes having a more detectable polling output signal when a desired event occurs, such as when the sample is present or when the sample volume is sufficient or insufficient. Improves includes having a more detectable polling output signal in comparison to the same polling output signal without one or more of the selected sensor strip properties. Improves includes having a more detectable polling output signal in comparison to other polling output signals. Improves includes having a more detectable polling output signal during one portion of the polling signal but not another portion, such as during the extended polling sequence but not the regular polling sequence.

Figure 10:
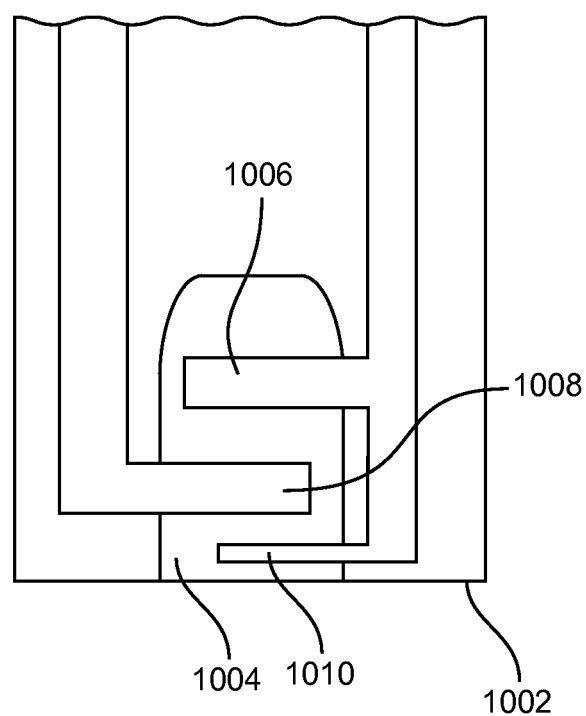
FIG. 10 depicts a schematic representation of a sensor strip used with a biosensor having an underfill recognition system.

FIG. 10 depicts a schematic representation of a sensor strip 1002 used with a biosensor having an underfill recognition system. The sensor strip 1002 forms a reservoir 1004. The sensor strip 1002 has a counter electrode 1006 and a working electrode 1008 positioned in the reservoir 1004. "Positioned in" includes partially or wholly in the reservoir, adjacent or near the reservoir, or like locations where the electrodes would electrically connect with a sample disposed in the reservoir. Counter electrode 1006 includes a sub-element 1010, which is positioned in the reservoir 1004 downstream of the working electrode 1008. A mediator is disposed between the counter electrode 1006 and the working electrode 1008. The mediator may be disposed on the counter electrode 1006, on the working electrode 1008, on the sensor strip 1002 in the reservoir 1004, a combination thereof, or the like. Other components have been omitted from the sensor strip 1002 for clarity. Other sensor strips maybe used including those with other and no mediators, no trigger electrodes, and other electrode arrangements. Other sensor strips maybe used including those with three electrodes and a second mediator, such as ferricyanide, on the third electrode.

The mediator used with the sensor strip 1002 may be selected to provide a first redox species at the counter electrode 1006 with a different redox potential than a second redox species at the sub-element 1010. The different redox potential also may be obtained by selecting electrodes with different material compositions and/or properties. While no mediator is used at the sub-element 1010, another mediator could be used to provide a different redox potential. When the polling signal is applied, the reduced forms of the lowest redox potential species are oxidized first or the oxidized forms of the highest redox species are reduced first depending on whether the redox reaction is oxidizing or reducing. When the redox reaction is reducing, a redox species with a higher redox potential is more easily reduced. When the redox reaction is oxidizing, a redox species with a lower redox potential is more easily oxidized. The different redox potentials may improve the regular and/or volume output signals, the accuracy and/or precision of the volume assessment and/or the analyte analysis, a combination thereof, or the like.

The mediator, M, may be a one electron transfer mediator or a multi-electron transfer mediator. One electron transfer mediators are chemical moieties capable of taking on one additional electron during the conditions of the electrochemical reaction. One electron transfer mediators include compounds, such as 1,1'-dimethyl ferrocene, ferrocyanide and ferricyanide, and ruthenium(III) and ruthenium(II) hexaamine. Multi-electron transfer mediators are chemical moieties capable of taking on more-than-one electron during the conditions of the reaction. Multi-electron transfer mediators include two electron transfer mediators, such as the organic quinones and hydroquinones, including phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Two electron transfer mediators also include the electro-active organic molecules described in U.S. Pat. Nos. 5,393,615; 5,498,542; and 5,520,786.

Two electron transfer mediators include 3-phenylimino-3H-phenothiazines (PIPT) and 3-phenylimino-3H-phenoxazines (PIPO). Two electron mediators also include the carboxylic acid or salt, such as ammonium salts, of phenothiazine derivatives. Two electron mediators further include (E)-2-(3H-phenothiazine-3-ylideneamino)benzene-1,4-disulfonic acid (Structure I), (E)-5-(3H-phenothiazine-3-ylideneamino)isophthalic acid (Structure II), ammonium(E)-3-(3H-phenothiazine-3-ylideneamino)-5-carboxybenzoate (Structure III), and combinations thereof. The structural formulas of these mediators are presented below. While only the di-acid form of the Structure I mediator is shown, mono- and di-alkali metal salts of the acid are included. The sodium salt of the acid may be used for the Structure I mediator. Alkali-metal salts of the Structure II mediator also may be used.

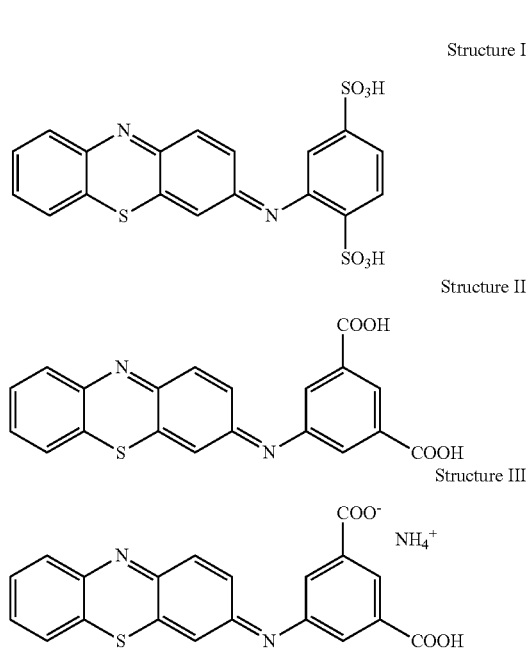

Two electron mediators may have redox potentials that are at least 100 mV lower, more preferably at least 150 mV lower, than ferricyanide. Other two electron mediators may be used. Other mediators and mediator combinations may be used including different mediators on the counter electrode 1006 and the sub-element 1010, a third mediator on a third electrode in a sensor strip having three electrodes, and the like.

In FIG. 10, the counter electrode 1006 and the sub-element 1010 have different redox potentials. Mediator, M, (not shown) creates a first redox potential at the counter electrode 1006. The sub-element 1010 lacks a mediator, and thus has a different redox potential. The different redox potentials may improve the polling output signals generated by a sample in the sensor strip. A volume threshold may be selected to better distinguish when a polling output signal is from a high or low redox species, and thus increase the differentiation between when a sample has sufficient volume (a full-fill condition) and when a sample has an insufficient volume (an under-fill condition), respectively.

Figure 11:
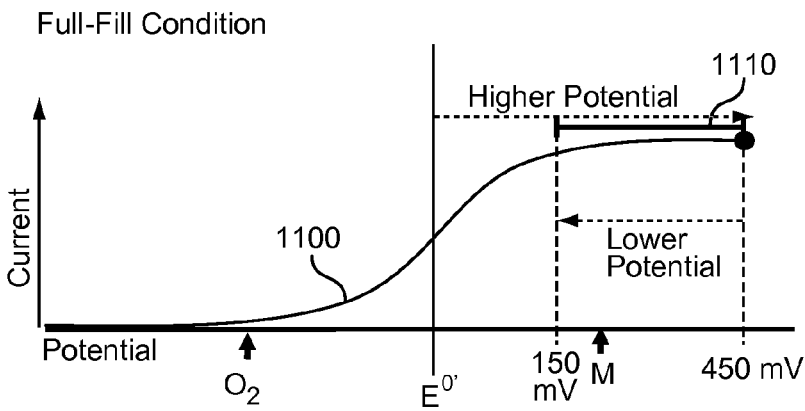
FIG. 11 depicts a graph of volume output signals generated in response to an extended polling sequence, illustrating a range of volume output signals that show a full-fill condition.
Figure 12:
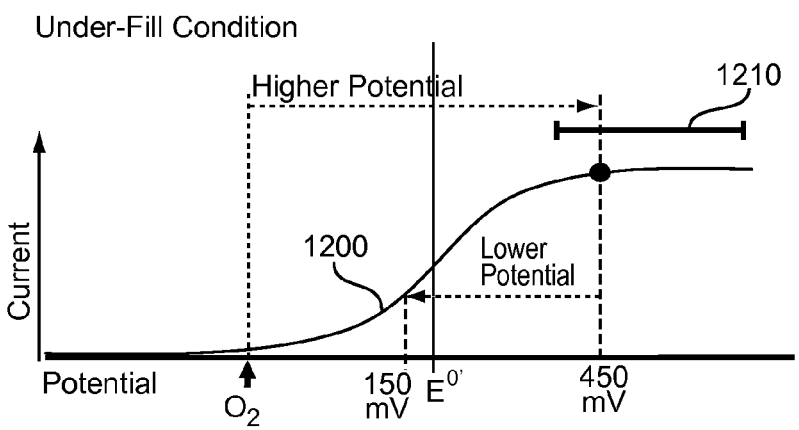
FIG. 12 depicts a graph of volume output signals generated in response to an extended polling sequence, illustrating a range of volume output signals that show an under-fill condition.

FIG. 11 and FIG. 12 depict graphs of the volume output signals that could be generated by a sample in the sensor strip 1002 of FIG. 10 in response to an extended polling sequence applied to a sensor strip. The sample is whole blood. The sensor strip is used in a biosensor having a gated amperometric test excitation signal. Thus, the extended polling sequence would be a potential and the volume output signals would be current. Other biosensors with the underfill recognition system may be used including those with other electrochemical and optical analyses. Other biological samples and analytes may be analyzed.

FIG. 11 illustrates a full-fill condition where the working electrode potential is compared to that of a counter electrode having a potential of about zero volts. The forward arrow indicates the higher polling potential, while the reverse arrow indicates the lower polling potential. M indicates the approximate potential position of the working electrode in the current-voltage curve based on the mediator, which in this case may be on the order of 0.2-0.25 V. The output currents obtained from the higher and lower extended polling potentials are obtained from curve 1100, and are virtually the same in relation to the curve, as both are generated from oxidation plateau 1110 of the mediator. $O_2$ indicates the approximate redox potential of oxygen in the sample (on the order of −0.3 to −0.5 V). However, as the reduction potential of $O_2$ is significantly lower than the reduction potential of the mediator, electrochemical coupling to the working electrode is dominated by the mediator on the counter electrode at full-fill condition.

FIG. 12 illustrates an under-fill condition where the sample covers the sub-element and working electrodes, but not the counter electrode. Thus, the working electrode potential is electrochemically coupled to the potential of the sub-element, and the counter electrode is not significantly participating in the electrochemistry. As the potential of the sub-element is substantially defined by the reduction potential of $O_2$, which is significantly lower than that of the mediator, the output currents obtained from the higher and lower extended polling potentials are shifted to the left along curve 1200 in relation to their positions on the curve 1100 in FIG. 11. As the lower potential moves left along the curve 1200 in FIG. 12, the corresponding output current moves away from oxidation plateau 1210, thus, providing a significantly lower output current. Thus, when the extended polling pulse is switched from higher potential to a lower potential in the under-filled condition of FIG. 12, a lower current may be generated from the lower potential in relation to a full-filled sensor, according to the voltammetric curve.

In FIG. 11 and FIG. 12 the higher potential may be from about 0.4 V to about 0.6 V. The higher potential also may be from about 0.4 V to about 0.5 V. The lower potential may be from about 0.1 V to about 0.3 V. The lower potential also may be from about 0.15 V to about 0.2 V. Other higher and lower potentials may be used, and the potentials may be selected in response to the reduction potential of the mediator. The higher and lower potentials also may be selected to provide the desired separation in the output currents.

In use, a sample of whole blood is placed in the reservoir 1004 of the sensor strip 1002. The biosensor applies the regular polling sequence of the polling signal to the sample. When the presence of the sample is detected, the biosensor transitions to the extended polling sequence as previously discussed. The sample generates volume output signals in response to the extended polling sequence. The biosensor detects whether the sample has insufficient or sufficient volume for analysis; whether there is an underfill condition or a full-fill condition.

When a sample (whole blood) covers the sub-element 1010 and the working electrode 1008 but not the counter electrode 1006, the sample has insufficient volume for analysis (an under-fill condition). Other criteria may be used for an underfill condition. Covers includes connecting, touching, having electrical communication, or the like. As oxidation occurs at the working electrode 1008, reduction occurs at the sub-element 1010. One such reduction is the reduction of oxygen present in the liquid sample of blood. Thus, the reduction of oxygen helps to generate a first extended output signal when the sensor strip 1002 has an underfill condition.

When a sample (whole blood) covers the sub-element 1010, the working electrode 1008, and the counter electrode 1006, the sample has sufficient volume for analysis (a full-fill condition). Other criteria may be used for a full-fill condition. The extended polling sequence reduces the mediator, M. The redox species of the mediator, M, at the counter electrode 1006 has a higher redox potential than the redox species of the oxygen at the sub-element 1010. Thus, the mediator reduction generates a second extended output signal that is different than the first extended output signal of the oxygen reduction.

Figure 13:
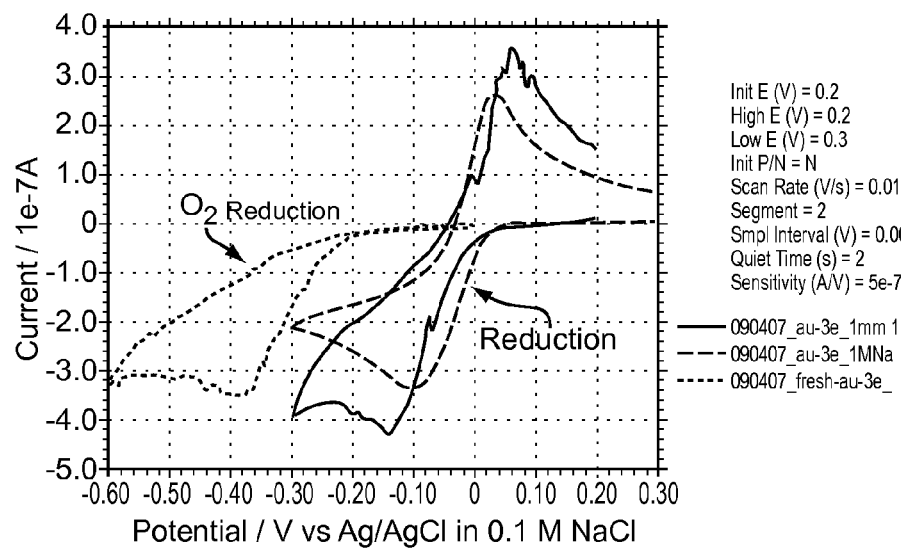
FIG. 13 depicts a graph illustrating output currents from the $O_2$ reduction and the mediator reduction in response to input potential.

FIG. 13 depicts cyclic voltammograms illustrating output currents from the oxygen reduction and the mediator reduction in response to an input potential. The input potential is in relation to a reference of Ag/AgCl in 0.1 M NaCl. The oxygen reduction generates very little if any positive current and essentially stops generating the anodic (oxidation) current as the potential increases from about −0.60 V to about 0 V. The current output from the mediator reduction transitions from negative to positive as the potential increases from about −0.30 V to about 0.30 V. When the sensor strip is under-filled, the working electrode is oxidizing the reduced mediator generated from the enzyme reaction, while the sub-element is reducing oxygen. This forms a complete redox reaction through the half cell reactions between the working electrode and the sub-element. While there is overlap of the current outputs from the oxygen reduction and the mediator reduction between about −0.30 V and about 0 V, the current outputs above about 0 V are essentially from the mediator reduction alone. Thus, a volume threshold may be selected responsive to an extended output polling signal including current outputs only from mediator reduction, or from a combination of mediator and oxygen reductions, such that the extended output polling signal includes current outputs only from the mediator reaction or from a combination of current outputs from the mediator and oxygen reactions. Other threshold volumes may be selected.

A volume threshold may be selected to differentiate the first extended output signals originating from the oxygen reduction from the second extended output signals originating from the reduction of the mediator, M. Differentiate includes volume thresholds that separate essentially all the first extended output signals from essentially all the second extended output signals. Differentiate includes volume thresholds that separate essentially all of the first extended output signals and less than all of the second extended output signals from the remainder of the second extended output signals. Differentiate includes volume thresholds that separate essentially all the second extended output signals and less than all of the first extended output signals from the remainder of the first extended output signals. Differentiate includes volume thresholds selected to improve the accuracy and/or precision of the biosensor and/or the volume assessment. Differentiate includes volume thresholds selected to distinguish the high and low redox potential species or the electrode potential. Differentiate includes volume thresholds selected to separate the first and second extended output signals in response to other criteria. Multiple volume thresholds may be selected to differentiate the polling output signals in response to the volume of the sample, three or more mediators or redox species, or other criteria.

A biosensor measures and compares the polling output signal to the volume threshold. When a polling output signal does not reach the volume threshold; this polling output signal is a first extended output signal, indicating the sample covers the sub-element 1010 and the working electrode 1008, but not the counter electrode 1006. Thus, the sample has insufficient volume for analysis; the sensor strip is under-filled. In contrast, when a polling output signal reaches the volume threshold; this polling output signal includes a second extended output signal, indicating the sample sufficiently covers the sub-element 1010, the working electrode 1008, and the counter electrode 1006. Thus, the sample has sufficient volume for analysis; the sensor strip is considered full-filled.

A simulation of a biosensor with an underfill recognition system shows that the presence of the redox couple is not necessary for the use of high and low polling potentials to determine whether the sample volume is sufficient. A redox couple on the sub-element and counter electrodes, such as the mediator and oxygen, may improve the volume output signals. However, the high and low redox potentials are not solely responsive to the redox couple.

In the simulation, high and low polling potentials were applied to a resistor of 1 MOhm. The high and low polling potentials are essentially the same as regular and extended polling sequences in a polling signal. The resistor simulates a sample in a sensor strip. The current flows simulate the volume output signals from the sample.

Figure 14:
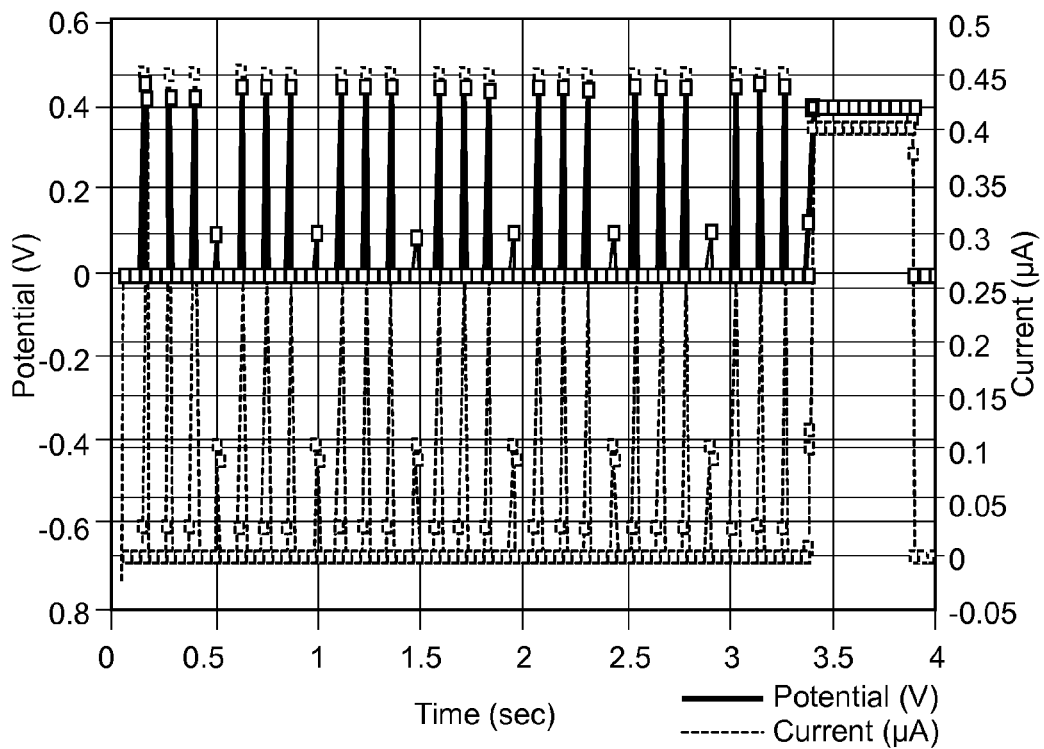
FIG. 14 depicts a plot of input and output signals used in a simulation.
Figure 15:
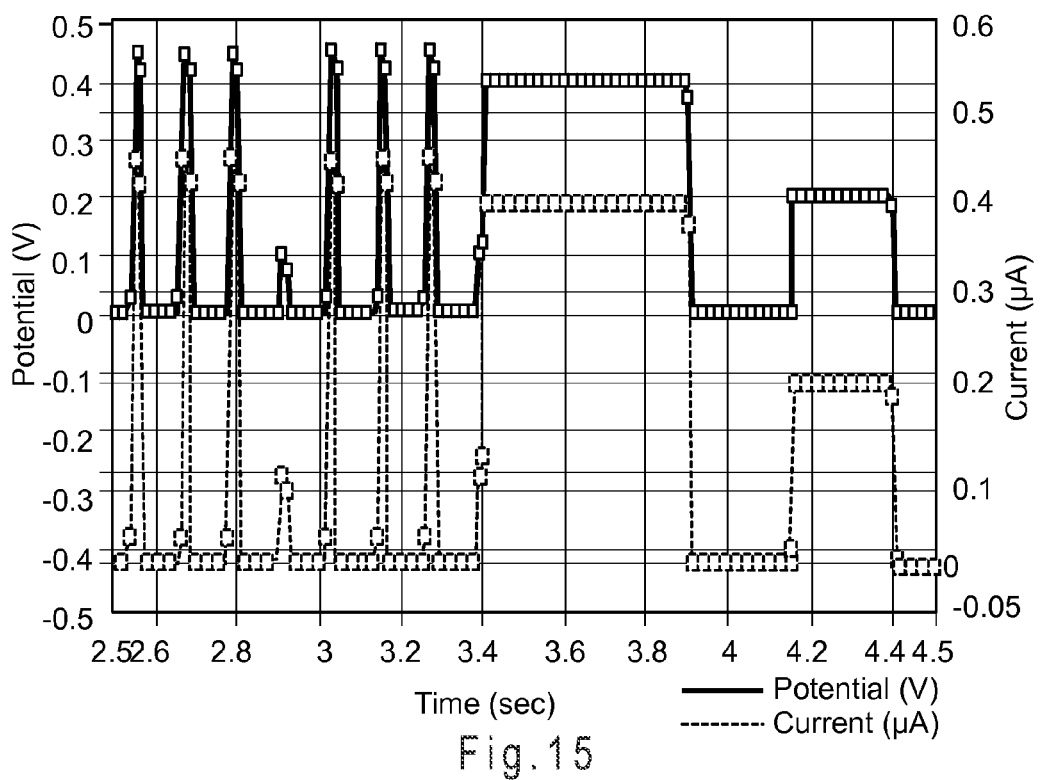
FIG. 15 depicts an expanded view of the last two cycles of the polling signal, test excitation signal, and output signals shown in FIG. 14.

FIG. 14 and FIG. 15 depict a plot of input and output signals used in the simulation. FIG. 14 depicts plots of the entire input and output signals used in the simulation. FIG. 15 depicts an expanded view of the last two cycles of the polling signals, the test excitation signal, and the output signals shown in FIG. 14. The input signals include the regular and extended polling sequences (potential), the test excitation signal (potential), the polling output signals (current), and the test output signal (current).

The simulation includes about seven cycles of regular and extended polling sequences before launching an assay potential or the test excitation signal. Each cycle includes two regular input pulses of the regular polling sequence and two extended input pulses of the extended polling sequence. The two regular input pulses of the regular polling sequence have regular amplitudes of 0.45 V. The extended polling sequence has a first extended input pulse with a high extended amplitude of 0.45 V and a second extended input pulse with a low extended amplitude of 0.1 V. The extended polling period is fixed at 0.25 sec. The regular and extended polling sequences each have a pulse width of 20 ms and a pulse interval of 100 ms. The sample rate is 100 points/sec.

The simulation applies the two pulses of the regular polling sequence. The presence of a "sample" is confirmed when the polling output signal (current) from the second regular input pulse (potential) of the regular polling sequence reaches a threshold of 0.13 µA. When a "sample" is present, the simulation applies the extended polling sequence. The simulation attempts six times (the first six cycles) to reach the threshold of 0.13 µA during the low extended amplitude of the second extended input pulse. The simulation fails during the first six cycles because the polling output signal from the low extended amplitude of the second pulses is only about 0.1 µA. During the seventh cycle, the simulation succeeds in reaching the threshold of 0.13 µA. The polling output signal (current) from the low extended amplitude of the second extended input pulse meets the threshold of 0.13 µA at about 3.4 sec. Thus, the simulation applies the test excitation signal immediately.

Figure 16:
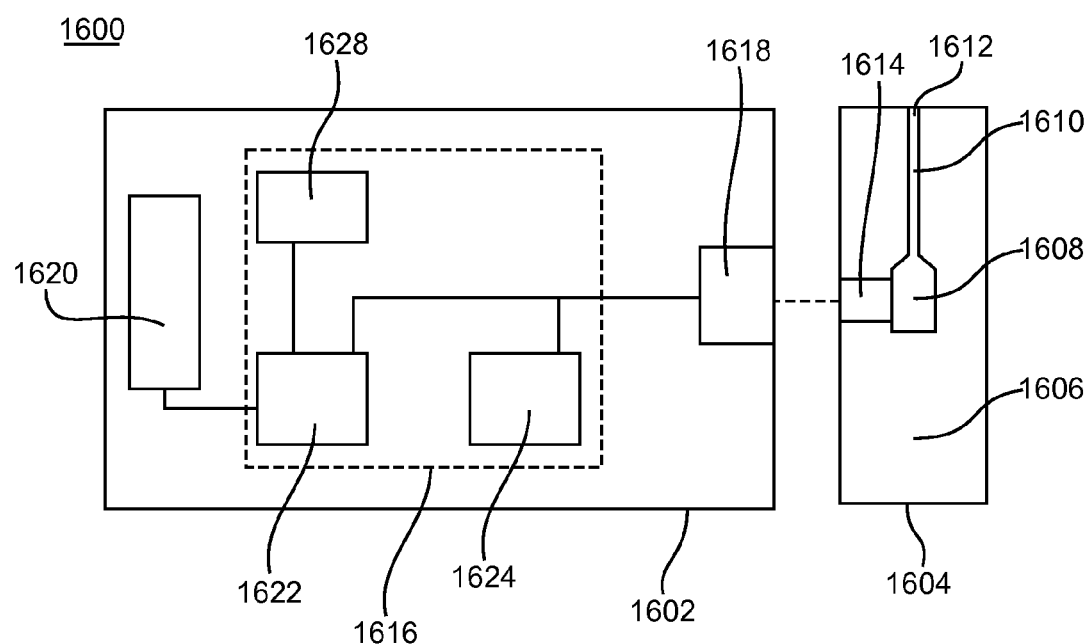
FIG. 16 depicts a schematic representation of a biosensor with an underfill recognition system.

FIG. 16 depicts a schematic representation of a biosensor 1600 with an underfill recognition system. Biosensor 1600 determines an analyte concentration in a sample of a biological fluid. The underfill recognition system indicates when a sample of the biological fluid has sufficient or insufficient volume or is large or not large enough, respectively, to provide an accurate and/or precise analysis of one or more analytes as previously discussed. Biosensor 1600 includes a measuring device 1602 and a sensor strip 1604, which may be implemented as a bench-top device, a portable or hand-held device, or the like. A handheld device is a device that may be held in a human hand and is portable. An example of a handheld device is the measuring device of the Ascensia® Elite Blood Glucose Monitoring System, available from Bayer HealthCare, LLC, Elkhart, Ind. The underfill recognition system may have other implementations in a biosensor.

Measuring device 1602 and sensor strip 1604 may be adapted to implement an electrochemical sensor system, an optical sensor system, a combination thereof, or the like. The underfill recognition system may improve the accuracy and/or precision of the biosensor 1600 in determining when underfill conditions occur, the analysis of one or more analyte, the volume assessment of the sample, or the like. Biosensor 1600 may be utilized to determine one or more analyte concentrations, such as alcohol, glucose, uric acid, lactate, cholesterol, bilirubin, free fatty acids, triglycerides, proteins, ketones, phenylalanine, enzymes, or the like, in a biological fluid, such as whole blood, urine, saliva, or the like. While a particular configuration is shown, biosensor 1600 may have other configurations, including those with additional components.

Sensor strip 1604 has a base 1606 that forms a reservoir 1608 and a channel 1610 with an opening 1612. Reservoir 1608 and channel 1610 may be covered by a lid with a vent. Reservoir 1608 defines a partially-enclosed volume. Reservoir 1608 may contain a composition that assists in retaining a liquid sample such as water-swellable polymers or porous polymer matrices. Reagents may be deposited in the reservoir 1608 and/or channel 1610. Reagents include one or more enzymes, mediators, binders, and other active or non-reactive species. Reagents include a chemical indicator for an optical system. Sensor strip 1604 may have a sample interface 1614 in electrical communication with the reservoir 1608. Sample interface 1614 may be located on the sensor strip 1604 to be conveniently accessed by a measuring device. Sensor strip 1604 may have other configurations.

The sample interface 1614 has conductors connected to a working electrode and a counter electrode. The electrodes may be substantially in the same plane. The electrodes may be disposed on a surface of the base 1606 that forms the reservoir 1608. The electrodes may extend or project into the volume formed by the reservoir 1608. A dielectric layer may partially cover the conductors and/or the electrodes. The counter electrode may have a sub-element or trigger electrode. The sub-element may be located upstream from the working electrode. The trigger electrode may be a third electrode. Mediator, M, may be disposed between the working and counter electrodes with no mediator between the trigger and the working electrodes, as previously discussed. Other or no mediators may be used. Sample interface 1614 may have other electrodes and conductors. Sample interface 1614 may have one or more optical portals or apertures for viewing the sample. Sample interface 1614 may have other components and configurations.

Measuring device 1602 includes electrical circuitry 1616 connected to a sensor interface 1618 and an optional display 1620. Electrical circuitry 1616 includes a processor 1622 connected to a signal generator 1624, and a storage medium 1628. Measuring device 1602 may have other components and configurations.

Signal generator 1624 provides electrical input signals to sensor interface 1618 in response to processor 1622. Electrical input signals may include the polling and test excitation signals used in the underfill recognition system. Electrical input signals may include electrical signals used to operate or control a detector and light source in the sensor interface 1618 for an optical sensor system. Electrical input signals may include a test excitation signal used in an electrochemical sensor system. The polling and test excitation signals for the underfill recognition system may be part of or incorporated with the test excitation signal for an electrochemical sensor system. Electrical input signals may be transmitted by the sensor interface 1618 to the sample interface 1614. Electrical input signals may be a potential or current and may be constant, variable, or a combination thereof, such as when an AC signal is applied with a DC signal offset. Electrical input signals may be applied as a single pulse or in multiple pulses, sequences, or cycles. Signal generator 1624 also may record signals received from the sensor interface 1618 as a generator-recorder.

Storage medium 1628 may be a magnetic, optical, or semiconductor memory, another processor readable storage device, or the like. Storage medium 1628 may be a fixed memory device or a removable memory device, such as a memory card.

Processor 1622 implements the underfill recognition system and data treatment using processor readable software code and data stored in the storage medium 1628. Processor 1622 starts the underfill recognition system in response to the presence of sensor strip 1604 at the sensor interface 1618, the application of a sample to the sensor strip 1604, user input, or the like. Processor 1622 directs the signal generator 1624 to provide electrical input signals to sensor interface 1618.

Processor 1622 receives and measures output signals from sensor interface 1618. Output signals may be electrical signals, such as current or potential, or light. Output signals include the polling and test output signals used in the underfill recognition system. Output signals include a test output signal generated in response to the redox reaction of the analyte in the sample. Output signals may be generated using an optical system, an electrochemical system, or the like. Polling output signals for the underfill recognition system may be part of or incorporated with the test output signal for an electrochemical sensor system. Processor 1622 may compare the polling output signals to one or more polling thresholds, as previously discussed.

Processor 1622 provides an error signal or other indication of an underfill condition when the polling output signal indicates the sample size is not large enough as previously discussed. Processor 1622 may display the error signal on the display 1620 and may store the error signal and related data in the storage medium 1628. Processor 1622 may provide the error signal at any time during or after the analyte analysis. Processor 1622 may provide the error signal when an underfill condition is detected and may prompt a user to add more of the biological fluid to the sensor strip 1604. Processor 1622 may stop the analyte analysis when an underfill condition is detected.

Processor 1622 determines analyte concentrations from the test output signals. The results of the analyte analysis are output to the display 1620 and may be stored in the storage medium 1628. Instructions regarding implementation of the analyte analysis may be provided by the processor readable software code stored in the storage medium 1628. The code may be object code or any other code describing or controlling the described functionality. The data from the analyte analysis may be subjected to one or more data treatments, including the determination of decay rates, K constants, slopes, intercepts, and/or sample temperature in the processor 1622.

Sensor interface 1618 has contacts that connect or electrically communicate with the conductors in the sample interface 1614 of the sensor strip 1604. Electrically communicate includes through wires, wirelessly, and the like. Sensor interface 1618 transmits the electrical input signals from the signal generator 1624 through the contacts to the connectors in the sample interface 1614. Sensor interface 1618 transmits output signals from the sample interface 1614 to the processor 1622 and/or the signal generator 1624. Sensor interface 1618 may include a detector, a light source, and other components used in an optical sensor system.

Display 1620 may be analog or digital. Display 1620 may be a LCD, a LED, a vacuum fluorescent, or other display adapted to show a numerical reading. Other displays may be used. The display 1620 electrically communicates with the processor 1622. The display 1620 may be separate from the measuring device 1602, such as when in wireless communication with the processor 1622. Alternatively, the display 1620 may be removed from the measuring device 1602, such as when the measuring device 1602 electrically communicates with a remote computing device, medication dosing pump, and the like.

In use, the biosensor 1600 activates and performs one or more diagnostic routines or other preparation functions prior to an analysis of a sample. Sensor strip 1604 is disposed to communicate with the measuring device 1602. Communicate with includes positions where the sample interface 1614 is in electrical and/or optical communication with the sensor interface 1618. Electrical communication includes the transfer of input and/or output signals between contacts in the sensor interface 1618 and conductors in the sample interface 1614. Optical communication includes the transfer of light between an optical portal in the sample interface 1614 and a detector in the sensor interface 1618. Optical communication includes the transfer of light between an optical portal in the sample interface 1614 and a light source in sensor interface 1618.

Sensor strip 1600 receives a liquid sample of a biological fluid. The sample is transferred into the volume formed by the reservoir 1608 by introducing the liquid to the opening 1612. The liquid sample flows through the channel 1610 into the reservoir 1608, filling the volume while expelling the previously contained air. The liquid sample chemically reacts with the reagents deposited in the channel 1610 and/or the reservoir 1608.

Biosensor 1600 may apply a regular polling sequence of a polling signal immediately when activated, immediately after the preparation functions are completed, after a selected time period, or when additional input or other action occurs, such as the placement of a sensor strip in communication with the measuring device 1602. Processor 1622 directs the signal generator 1624 to provide the regular polling sequence of the polling signal to the sensor interface 1618, which applies the regular polling sequence to the sample through the electrodes in the sample interface 1614. Signal generator 1624 cycles through one or more regular polling periods as directed by the processor 1622, applying the regular polling sequence to the reservoir 1608 in the sensor strip 1604. When a sample is present in the reservoir 1608, the sample generates a sample output signal in response to the regular polling sequence.

Processor 1622 detects when a sample of the biological fluid is present or not present for analysis. Sample interface 1614 provides the sample output signal to the sensor interface 1618. Processor 1622 receives the sample output signal from the sensor interface 1618. Processor 1622 may show the sample output signal on the display 1620 and/or may store the sample output signal in the storage medium 1628. Processor 1622 detects a sample is present when the sample polling output signal reaches one or more sample thresholds. Processor 1622 detects a sample is not present when the sample polling output signal does not reach one or more sample thresholds.

Signal generator 1624 transitions from the regular polling sequence to the extended polling sequence as directed by the processor 1622 when a sample is present. Processor 1622 may stop the regular polling sequence and apply the extended polling sequence to the sample immediately or after a selected time period. Processor 1622 directs the signal generator 1624 to provide the extended pulse sequence to the sensor interface 1618, which applies the extended pulse sequence to the sample through the electrodes in the sample interface 1614. The sample generates a volume output signal in response to the extended polling sequence.

Processor 1622 detects when the sample of the biological fluid has sufficient or insufficient volume for analysis. Sample interface 1614 provides the volume output signal to the sensor interface 1618. Processor 1622 receives the volume output signal from the sensor interface 1618. Processor 1622 may show the volume output signal on the display 1620 and/or may store the volume output signal in the storage medium 1628. Processor 1622 compares the volume output signal with one or more volume thresholds. Processor 1622 detects a sample has sufficient volume or a full-fill condition when the volume polling output signal reaches one or more volume thresholds. Processor 1622 detects a sample has insufficient volume or an underfill condition when the volume polling output signal does not reach one or more volume thresholds.

When the sample volume is not sufficient for analysis, the processor 1622 may request a user to add more sample, restart the regular polling sequence, enter a sleep more, stop the test excitation signal, a combination thereof, or the like. When in a sleep mode, the processor 1622 restarts the regular polling sequence when additional input is received, such as the addition of more sample. To restart the regular polling sequence, the processor 1622 directs the signal generator 1624 to apply the regular polling sequence of the polling signal to the sensor interface 1618, which applies the regular polling sequence to the sample through the electrodes in the sample interface 1614. Processor 1622 may deactivate or may cycle through regular polling sequences for as long as a volume output signal does not meet one or more volume thresholds, for a fixed time period, for a selected number of cycles, a combination thereof, or the like.

Processor 1622 may prompt a user to add more biological fluid to the sensor strip 1604 prior to proceeding with the analysis of the analyte. Processor 1622 may provide an error signal or other indicator of an underfill condition when the volume output signal indicates the sample size is not large enough. The error signal may be shown on the display 1620 and/or retained in the storage medium 1628. The error signal may include a request or symbol requesting additional sample from a user. Processor 1622 may provide the error signal immediately or another time.

When more sample is present in the reservoir 1608, the larger sample generates another sample output signal in response to the regular polling sequence. Processor 1622 detects more sample is present when the other sample output signal reaches the same or another sample threshold.

When the presence of more sample is detected, the processor 1622 stops the regular polling sequence and applies the extended polling sequence to the larger sample. The larger sample generates another volume polling output signal in response to the extended polling sequence. Processor 1622 the compares the other volume output signal with one or more volume thresholds. The other volume output signal may indicate a sufficient sample volume (full-fill condition) or an insufficient sample volume (underfill condition) when the other volume output signal does or does not reach, respectively, one or more volume thresholds. If the sample volume is insufficient for analysis after a second filling, the processor 1622 may repeat the previous procedures a selected number of times or until sufficient volume is obtained, stop the testing, or the like.

When the processor 1622 detects the sample has sufficient volume for analysis, the processor 1622 directs the signal generator 1624 to apply the test excitation signal to the sample. Sensor interface 1618 applies the test excitation signal to the sample through the sample interface 1614 during a test period. The sample generates a test output signal in response to the test excitation signal. The sample interface 1614 provides the test output signal to the sensor interface 1618.

Processor 1622 may direct the signal generator 1624 to apply the test excitation signal to the sensor interface 1618 when the volume output signal reaches one or more volume thresholds. Processor 1622 may have comparator circuitry to provide the test excitation signal to the sensor interface 1618 when the volume output signal reaches one or more volume thresholds. In the comparator circuitry, the volume output signal may be directed into the input of an electrical (analog) comparator or the like. The comparator compares the volume output signal with a volume threshold value. When the polling output signal is equal to or greater or only greater than the volume threshold value, the output of the comparator triggers the launch of the test excitation signal.

When the sample volume is sufficient for analysis, the processor 1622 directs the signal generator 1624 to apply the test excitation signal to the sensor interface 1618. In an optical system, the sensor interface 1618 provides the electrical input signals to operate the detector and light source. Sensor interface 1618 receives the test output signal from the detector. In an electrochemical system, the sensor interface 1618 applies the test excitation signal to the sample through the sample interface 1614. The test excitation signal for the underfill recognition system may be part of or incorporated with the test excitation signal. The sample generates a test output signal from the redox reaction of the analyte in response to the test excitation signal. Sample interface 1614 provides the test output signal to the sensor interface 1618.

The sample generates one or more test output signals in response to the test excitation signal. Processor 1622 receives a test output signal from the sensor interface 1618. Processor 1622 measures the test output signal generated by the sample. Processor 1622 may show the test output signal on the display 1620 and/or may store test output signal in the storage medium 1628. The biosensor 1600 determines one or more analyte concentrations in the sample in response to the one or more test output signals.

Processor 1622 receives the test output signal from the sensor interface 1618. Processor 1622 determines the analyte concentration of the sample in response to the test output signal. Processor 1622 may show the test output signal on the display 1620 and/or may store the test output signal in the storage medium 1628.

Without limiting the scope, application, or implementation, the methods and systems previously described may be implemented using an algorithm, such as the following:

Step 1: Turn on biosensor power.

Step 2: Perform biosensor self-test and electronics standardization.

Step 3: Take initial temperature and other measurements.

Step 4: Start regular polling pulse sequence at a selected frequency, regular input pulse width, and regular input pulse amplitude.

Step 5: Check sample output signal(s) from regular polling pulse sequence.

If s<sample threshold, continue on regular polling pulse sequence (Step #4).

If s≥sample threshold, then repeat the same check within 5 msec.

If repeated s<sample threshold, continue on regular polling pulse sequence (Step #4).

If repeated s≥sample threshold, then go to extended polling pulse sequence at a fixed time.

Step 6: Start extended polling pulse sequence: first extended input pulse at first extended amplitude; second extended input pulse at second extended amplitude.

Step 7: Start time 0 counting $t_{ext}$ for the duration of extended polling period.

Step 8: Check volume output signal (v) from extended polling pulse sequence at second extended amplitude of second extended input pulse.

If v<volume threshold, go back to regular polling pulse sequence (Step #4).

If v≥volume threshold, then repeat the same check within 5 msec.

If repeated v<volume threshold, then go back to regular polling pulse sequence (Step #4).

If repeated v≥volume threshold, then start the test excitation signal.

Step 9: If $t_{ext}$>1 sec, start additional prompt in user interface to alert user of adding more sample.

Step 10: If $t_{ext}$>60 sec, display error "insufficient sample".

While various embodiments of the invention have been described, it will be apparent to those of ordinary skill in the art that other embodiments and implementations are possible within the scope of the invention.

What is claimed is:

1. A method for assessing the volume of a sample in a biosensor, comprising:
applying a regular polling sequence, where the regular polling sequence substantially eliminates irreversible alteration of the concentration of at least one analyte in the sample during the application of the regular polling sequence;
detecting the presence of the sample;
then applying an extended polling sequence having at least one different extended input pulse, where the extended polling sequence substantially eliminates irreversible alteration of the concentration of the at least one analyte in the sample during the application of the extended polling sequence;
detecting whether a sample volume is sufficient for analysis of the at least one analyte in the sample; and
applying a test excitation signal when the sample volume is sufficient for analysis of the at least one analyte in the sample, where the test excitation signal irreversibly alters the concentration of the at least one analyte in the sample during the application of the test excitation signal.

2. The method of claim 1, further comprising determining the concentration of the at least one analyte in the sample.

3. The method of claim 1, where the regular and extended polling sequences and the test excitation signal are part of a gated amperometry electrochemical analysis.

4. The method of claim 1, the test excitation signal having at least one test input pulse with a test amplitude that is essentially the same as a regular amplitude of at least one regular input pulse of the regular polling sequence.

5. The method of claim 1, further comprising detecting at least one of a selected volume and a range of volumes.

6. The method of claim 1, where a last pulse in the extended polling sequence is a different extended pulse.

7. The method of claim 1,
the regular polling sequence having at least one regular input pulse; and
the extended polling sequence having at least one similar extended input pulse, where the at least one similar extended input pulse has an extended amplitude that is essentially the same as a regular amplitude of the at least one regular input pulse, and
where the at least one different extended pulse has another extended amplitude that is not the same as the regular amplitude of the at least one regular input pulse.

8. The method of claim 1,
the regular polling sequence having at least one regular input pulse; and
the extended polling sequence having at least one cycle, where each cycle has at least one similar extended input pulse and at least one different extended input pulse.

9. The method of claim 8, where the at least one similar extended input pulse has an extended amplitude that is essentially the same as a regular amplitude of the at least one regular input pulse, and where the at least one different extended pulse has another extended amplitude that is not the same as the regular amplitude of the at least one regular input pulse.

10. The method of claim 8, where a last pulse in each cycle is a different extended pulse.

11. The method of claim 1, further comprising:
counting a delay period when sample volume is insufficient; and
detecting whether a sample volume is sufficient for analysis of the at least one analyte in the sample after the delay period.

12. The method of claim 1, further comprising indicating when the sample volume is insufficient for analysis of the at least one analyte in the sample.

13. The method of claim 12, further comprising:
stopping the test excitation signal when the sample volume is insufficient for analysis of the at least one analyte in the sample;
requesting a user to add more sample;
applying another regular polling sequence, where the another regular polling sequence substantially eliminates irreversible alteration of the concentration of the at least one analyte in the sample during the application of the another regular polling sequence;
detecting the presence of a larger sample;
applying another extended polling sequence having at least one different extended input pulse to the larger sample, where the another extended polling sequence substantially eliminates irreversible alteration of the concentration of the at least one analyte in the sample during the application of the another extended polling sequence; and
detecting whether the larger sample has a sample volume sufficient for analysis of the at least one analyte in a sample.

14. The method of claim 1, further comprising improving at least one of a sample output signal and a volume output signal with at least one mediator.

15. The method of claim 14, where the at least one mediator includes a two electron transfer mediator.

16. A method for assessing the volume of a sample in a biosensor, comprising:
applying a regular polling sequence, where the regular polling sequence substantially eliminates irreversible alteration of the concentration of at least one analyte in the sample during the application of the regular polling sequence;
detecting when at least one regular output pulse reaches at least one sample threshold;

applying an extended polling sequence, where the extended polling sequence substantially eliminates irreversible alteration of the concentration of the at least one analyte in the sample during the application of the extended polling sequence;

detecting when at least one different extended output pulse reaches at least one volume threshold;

indicating when a sample volume is insufficient for analysis of the at least one analyte in the sample; and then applying a test excitation signal when the sample volume is sufficient for analysis of at least one analyte in the sample, where the test excitation signal irreversibly alters the concentration of the at least one analyte in the sample during the application of the test excitation signal.

17. The method of claim 16, where a last pulse in the extended polling sequence is a different extended pulse.

18. The method of claim 16, further comprising:
applying at least one similar extended input pulse with an extended amplitude that is essentially the same as a regular amplitude of the at least one regular input pulse; and applying at least one different extended pulse with another extended amplitude that is not the same as the regular amplitude of the at least one regular input pulse.

19. The method of claim 18, further comprising applying a test excitation signal having at least one test input pulse with a test amplitude that is essentially the same as the regular amplitude of the at least one regular input pulse.

20. The method of claim 16, the extended polling sequence having at least one cycle, where each cycle has at least one similar extended input pulse and at least one different extended input pulse.

21. The method of claim 20, where the at least one similar extended input pulse has an extended amplitude that is essentially the same as a regular amplitude of the at least one regular input pulse, and where the at least one different extended pulse has another extended amplitude that is not the same as the regular amplitude of the at least one regular input pulse.

22. The method of claim 20, where a last pulse in each cycle is a different extended pulse.

23. The method of claim 16, further comprising:
detecting an initial extended output pulse that does not reach at least one or more volume thresholds;
counting a delay period from the initial extended output pulse; and
detecting a later extended output pulse after the delay period that does reach one or more volume thresholds.

24. The method of claim 16, further comprising:
stopping the test excitation signal when the sample volume is insufficient for analysis of the at least one analyte in the sample;
requesting a user to add more sample
applying another regular polling sequence to a larger sample, where the another regular polling sequence substantially eliminates irreversible alteration of the concentration of the at least one analyte in the sample during the application of the another regular polling sequence;
detecting when at least one regular output pulse from the larger sample reaches at least one sample threshold;
applying another extended polling sequence to the larger sample, where the another extended polling sequence substantially eliminates irreversible alteration of the concentration of the at least one analyte in the sample during the application of the another extended polling sequence; and
detecting when at least one different extended output pulse from the larger sample reaches at least one volume threshold.

25. The method of claim 16, further comprising improving at least one of a sample output signal and a volume output signal with at least one mediator.

26. The method of claim 25, where the at least one mediator comprises a two electron transfer mediator.

27. The method of claim 16, further comprising determining the concentration of at least one analyte in a sample.

28. The method of claim 27, where the regular and extended polling sequences and the test excitation signal are part of a gated amperometry electrochemical analysis.

* * * * *

UNITED STATES PATENT AND TRADEMARK OFFICE
CERTIFICATE OF CORRECTION

| | | |
|---|---|---|
| PATENT NO. | : 8,668,819 B2 | Page 1 of 1 |
| APPLICATION NO. | : 12/910449 | |
| DATED | : March 11, 2014 | |
| INVENTOR(S) | : Huan-Ping Wu et al. | |

It is certified that error appears in the above-identified patent and that said Letters Patent is hereby corrected as shown below:

IN THE SPECIFICATION
In Column 32, Line 28, delete "Sensor strip 1600" and insert -- Sensor strip 1604 --, therefor.

IN THE CLAIMS
In Column 38, Line 13, in Claim 24, delete "sample" and insert -- sample; --, therefor.

Signed and Sealed this
Twenty-ninth Day of September, 2015

Michelle K. Lee
*Director of the United States Patent and Trademark Office*